United States Patent
Demers et al.

(10) Patent No.: US 10,358,431 B1
(45) Date of Patent: *Jul. 23, 2019

(54) ANTIMICROBIALS FROM AN EPIGENETICS BASED FUNGAL METABOLITE SCREENING PROGRAM

(71) Applicants: Danielle H. Demers, Gaithersburg, MD (US); Bill J. Baker, Temple Terrace, FL (US); Ala Azhari, Tampa, FL (US); Renee M. Fleeman, Austin, TX (US); Dennis E. Kyle, Athens, GA (US); Lindsey Neil Shaw, Tampa, FL (US)

(72) Inventors: Danielle H. Demers, Gaithersburg, MD (US); Bill J. Baker, Temple Terrace, FL (US); Ala Azhari, Tampa, FL (US); Renee M. Fleeman, Austin, TX (US); Dennis E. Kyle, Athens, GA (US); Lindsey Neil Shaw, Tampa, FL (US)

(73) Assignees: University of South Florida, Tampa, FL (US); King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/023,627

(22) Filed: Jun. 29, 2018

Related U.S. Application Data

(60) Division of application No. 15/675,328, filed on Aug. 11, 2017, which is a continuation-in-part of application No. 15/220,777, filed on Jul. 27, 2016, now abandoned.

(60) Provisional application No. 62/197,233, filed on Jul. 27, 2015.

(51) Int. Cl.
*C07D 311/58* (2006.01)
*C07C 65/40* (2006.01)
*C07C 49/757* (2006.01)
*C07J 1/00* (2006.01)
*C07C 65/19* (2006.01)

(52) U.S. Cl.
CPC .......... *C07D 311/58* (2013.01); *C07C 49/757* (2013.01); *C07C 65/19* (2013.01); *C07C 65/40* (2013.01); *C07J 1/00* (2013.01)

(58) Field of Classification Search
CPC ..... C07D 311/58; C07C 49/757; C07C 65/19; C07C 65/40; C07J 1/00
USPC ....................................................... 549/405
See application file for complete search history.

(56) References Cited

U.S. PATENT DOCUMENTS

| | | | | |
|---|---|---|---|---|
| 3,546,073 | A * | 12/1970 | Holmlund | C07C 47/565 |
| | | | | 435/123 |
| 5,420,334 | A * | 5/1995 | Singh | A61K 31/12 |
| | | | | 560/138 |
| 10,144,719 | B1 * | 12/2018 | Demers | C07D 311/58 |

FOREIGN PATENT DOCUMENTS

WO   WO2002074725   *   9/2002

OTHER PUBLICATIONS

Ellestad; Tetrahedron 1969, 25, 1323-1334. (Year: 1969).*

(Continued)

*Primary Examiner* — Daniel R Carcanague
(74) *Attorney, Agent, or Firm* — Michele L. Lawson; Smith & Hopen, P.A.

(57) ABSTRACT

Novel antimicrobial compounds against drug targets such as Eskape pathogens, *Leishmania donovani, Mycobacterium tuberculosis, Clostridium difficile, Naegleria fowleri*, and cancer are presented herein.

8 Claims, 13 Drawing Sheets

Specification includes a Sequence Listing.

1

2

3      4

5

6

(56) References Cited

OTHER PUBLICATIONS

Mogi; Biochimica et Biophysica Acta 1787 (2009) 129-133. (Year: 2009).*
Nazoe; Tetrahedron 1971, 27, 6063-6071. (Year: 1971).*
Singh; J. Org. Chem. 1996, 61, 7727-7737. (Year: 1996).*

* cited by examiner

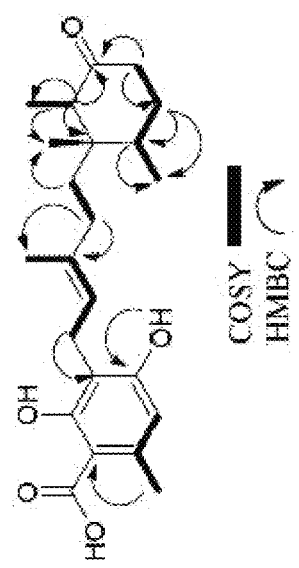
Figure 12
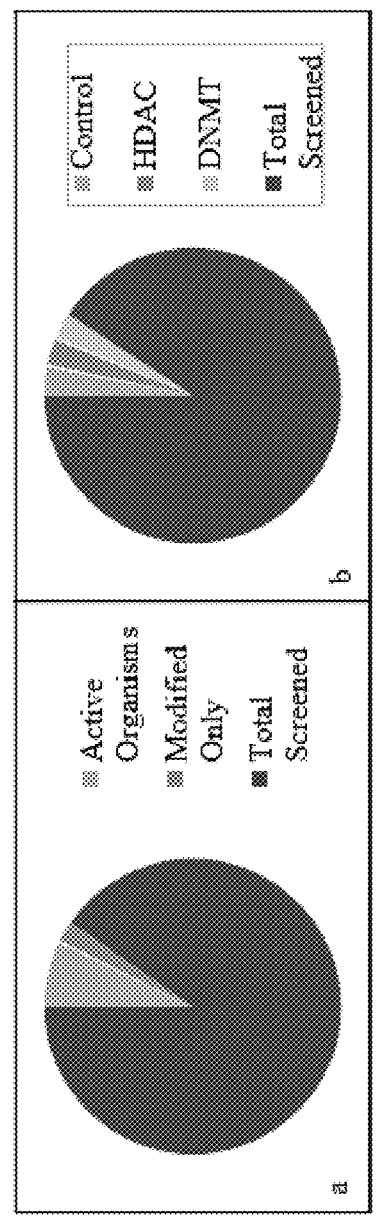
Figure 13A-B

ANTIMICROBIALS FROM AN EPIGENETICS BASED FUNGAL METABOLITE SCREENING PROGRAM

CROSS REFERENCE TO RELATED APPLICATIONS

This application is a divisional of and claims priority to U.S. Nonprovisional application Ser. No. 15/675,328, entitled "Antimicrobials from an Epigenetics Based Fungal Metabolite Screening Program", filed Aug. 11, 2017, which is a continuation in part of and claims priority to U.S. Nonprovisional application Ser. No. 15/220,777, entitled "Antimicrobials from an Epigenetics Based Fungal Metabolite Screening Program", filed Jul. 27, 2016, which is a nonprovisional of and claims priority to U.S. Provisional Patent Application No. 62/197,233, entitled "Antimicrobials from an Epigenetics Based Fungal Metabolite Screening Program", filed Jul. 27, 2015, the entire contents of each of which is herein incorporated into this disclosure.

GOVERNMENTAL SUPPORT

This invention was made with Government support under Grant No. AI103715 awarded by the National Institutes of Health (NIH) and Grant No. AI103673 awarded by the National Institute of Allergy and Infectious Diseases (NI-AID). The Government has certain rights in the invention.

FIELD OF INVENTION

This invention relates to antimicrobials. Specifically, the invention provides new antimicrobials that are effective against various drug targets such as Eskape pathogens, *Leishmania donovani*, *Mycobacterium tuberculosis*, *Clostridium difficile*, *Naegleria fowleri*, and cancer.

BACKGROUND OF THE INVENTION

Sedentary and microbial organisms in all environments—marine, terrestrial, and fresh water—must produce secondary metabolites with which they can interact with the world around them. Micro-environments, such as fresh water ponds, inner-city forests, or coastal estuaries, to name a few, may be home to countless organisms that must respond to incredibly localized stressors that make no two environments exactly the same. New chemical structures are emerging all the time from countless environmental sources, and as threats to human health evolve, it could certainly be argued that natural products research is the way forwards.

Thanks to genomic advancements, it is clear that micro-organisms cultured in the lab routinely produce only a fraction of the secondary metabolites that are coded for in their DNA. (Gross, H. Strategies to Unravel the Function of Orphan Biosynthesis Pathways: Recent Examples and Future Prospects. *Applied Microbiology and Biotechnology.* 2007, pp 267-277). This is accomplished by the regulation of transcription by enzymes activated and deactivated based on environmental factors. (Bok, J. W.; Keller, N. P. LaeA, a Regulator of Secondary Metabolism in *Aspergillus* Spp. *Eukaryot. Cell* 2004, 3 (2), 527-535). In filamentous fungi, it is known that most secondary metabolite genes are clustered to allow for the most efficient regulation and these clusters can be activated or deactivated by culture conditions, resulting in vastly different metabolite production. (Bok, J. W.; Keller, N. P. LaeA, a Regulator of Secondary Metabolism in *Aspergillus* Spp. *Eukaryot. Cell* 2004, 3 (2), 527-535; Keller, N. P.; Hohn, T. M. REVIEW Metabolic Pathway Gene Clusters in Filamentous Fungi. *Fungal Genet. Biol.* 1997, 21, 17-29).

Once isolated, a micro-organism of interest can be cultured in the lab under any number of easily accessible stressors that can change secondary metabolite production. Culture variations can be as simple as changing the shape of the culture vessel, or as complex as the addition of biological material from another microbe or host organism. In this way, a single strain can produce a multitude of different compounds. (Gross, H. Strategies to Unravel the Function of Orphan Biosynthesis Pathways: Recent Examples and Future Prospects. *Applied Microbiology and Biotechnology.* 2007, pp 267-277; Lim, F. Y.; Sanchez, J. F.; Wang, C. C. C.; Keller, N. P. Toward Awakening Cryptic Secondary Metabolite Gene Clusters in Filamentous Fungi. *Methods Enzymol.* 2012, 517, 303-324; Brakhage, A. A.; Schroeckh, V. Fungal Secondary Metabolites—Strategies to Activate Silent Gene Clusters. *Fungal Genet. Biol.* 2011, 48 (1), 15-22; Bode, H. B.; Bethe, B.; Hofs, R.; Zeeck, A. Big Effects from Small Changes: Possible Ways to Explore Nature's Chemical Diversity. *ChemBioChem* 2002, 3 (7), 619-627; Scherlach, K.; Hertweck, C. Triggering Cryptic Natural Product Biosynthesis in Microorganisms. *Org. Biomol. Chem.* 2009, 7 (9), 1753-1760). While this 'OSMAC' ('One Strain Many Compounds') strategy is extremely useful in exploiting the full biosynthetic potential of a micro-organism of interest, it is rather intensive in time and consumables. (Bode, 2002).

Rather than systematically changing culture conditions, the biosynthetic potential of a micro-organism of interest can also be explored through whole genome sequencing. Many secondary metabolites are products of known biosynthetic pathways. The ability to ascribe a product to the genes that code for it allows for the unique ability to analyze a whole genome and predict the metabolites that can be produced. Culture conditions curated to that biosynthetic pathway can then be employed to isolate specific compounds of interest. (Bromann, K.; Toivari, M.; Viljanen, K.; Vuoristo, A.; Ruohonen, L.; Nakari-Setälä, T. Identification and Characterization of a Novel Diterpene Gene Cluster in *Aspergillus nidulans. PLoS One* 2012, 7 (4); Bergmann, S.; Schümann, J.; Scherlach, K.; Lange, C.; Brakhage, A. A.; Hertweck, C. Genomics—Driven Discovery of PKS—NRPS Hybrid Metabolites from *Aspergillus nidulans. Nat. Chem. Biol.* 2007, 3 (4), 213-217; Scherlach, K.; Hertweck, C. Discovery of Aspoquinolones A-D, Prenylated Quinoline-2-One Alkaloids from *Aspergillus nidulans*, Motivated by Genome Mining. *Org. Biomol. Chem.* 2006, 4, 3517-3520; Van Lanen, S. G.; Shen, B. Microbial Genomics for the Improvement of Natural Product Discovery. *Curr. Opin. Microbiol.* 2006, 9 (3), 252-260; Cone, C.; Challis, G. L. New Natural Product Biosynthetic Chemistry Discovered by Genome Mining. *Nat. Prod. Rep.* 2009, 26 (8), 977-986; Challis, G. L. Mining Microbial Genomes for New Natural Products and Biosynthetic Pathways. *Microbiology* 2008, 154 (6), 1555-1569).

Genome mining and the OSMAC approach are both useful techniques for the discovery of the biosynthetic potential of a single organism. If, however, you have a microbial library that you would like to screen, these techniques may not be the most efficient. Epigenetic modification—that is, the use of small molecule enzyme inhibitors to promote the expression and prevent the silencing or down-regulation of secondary metabolite gene clusters can be used as a more ubiquitous technique to exploit the biosynthetic potential of a larger number of microorganisms. (Williams, R. B.; Henrikson, J. C.; Hoover, A. R.; Lee, A. E.;

Cichewicz, R. H. Epigenetic Remodeling of the Fungal Secondary Metabolome. *Org Biomol Chem* 2008, 6 (11), 1895-1897; Cichewicz, R. H. Epigenome Manipulation as a Pathway to New Natural Product Scaffolds and Their Congeners Robert. *Nat. Prod. Rep.* 2010, 27 (1), 11-22; Henrikson, J. C.; Hoover, A. R.; Joyner, P. M.; Cichewicz, R. H. A Chemical Epigenetics Approach for Engineering the in Situ Biosynthesis of a Cryptic Natural Product from *Aspergillus niger*. *Org. Biomol. Chem.* 2009, 7 (3), 435-438; Wang, X.; Sena Filho, J. G.; Hoover, A. R.; King, J. B.; Ellis, T. K.; Powell, D. R.; Cichewicz, R. H. Chemical Epigenetics Alters the Secondary Metabolite Composition of Guttate Excreted by an Atlantic-Forest-Soil-Derived *Penicillium citreonigrum*. *J. Nat. Prod.* 2010, 73 (5), 942-948). Histone deacetylase (HDAC) and DNA methyltransferase (DNMT) inhibitors can be used as culture additives to epigenetically 'turn on' secondary metabolite gene clusters in a library of filamentous fungi for the maximum surveying of bioactive natural product potential therein. (Beau, J.; Mahid, N.; Burda, W. N.; Harrington, L.; Shaw, L. N.; Mutka, T.; Kyle, D. E.; Barisic, B.; Van Olphen, A.; Baker, B. J. Epigenetic Tailoring for the Production of Anti-Infective Cytosporones from the Marine Fungus Leucostoma persoonii. *Mar. Drugs* 2012, 10 (4), 762-774).

There are many different techniques available for natural products drug discovery efforts. While exploring the biosynthetic potential of a single organism can be very lucrative, screening efforts are needed in order to identify those "lead" organisms. With a robustly designed screening program, natural product extracts from a multitude of sources can be screened side by side in high-throughput capable bioassays against a wide variety of disease targets. The resulting diversity of bioactivity information combined with metabolite profiling can afford intense prioritization of extracts at a very early stage, streamlining further chemical investigation to a highly time and cost effective level of efficiency.

Drug Discovery Targets

Natural products isolation efforts largely follow the same generic scheme (FIG. 1). Efforts aimed at drug discovery can take place at any of the stages, from extraction to pure compound isolation. There are pros and cons to each approach, though it is generally accepted that the earlier the efforts can be prioritized, the better.

Crude extracts can contain thousands of compounds, however, it is possible to get useful information from that complex mixture in a high-throughput way. Metabolite profiling of crude extracts can be used for initial dereplication and more advanced matabolomic analysis can reveal chemical outliers that may be of interest. (Sica, V. P.; Raja, H. A.; El-Elimat, T.; Kertesz, V.; Van Berkel, G. J.; Pearce, C. J.; Oberlies, N. H. Dereplicating and Spatial Mapping of Secondary Metabolites from Fungal Cultures in Situ. *J. Nat. Prod.* 2015, 78 (8), 1926-1936; Kellogg, J. J.; Todd, D. A.; Egan, J. M.; Raja, H. A.; Oberlies, N. H.; Kvalheim, O. M.; Cech, N. B. Biochemometrics for Natural Products Research: Comparison of Data Analysis Approaches and Application to Identification of Bioactive Compounds. *J. Nat Prod.* 2016, 79 (2), 376-386). High-throughput bioassays that are tolerant of complex mixtures can be used to discover and prioritize activity early in the investigation process. More sensitive and selective bioassays that are not tolerant of complex mixtures would require more purified fractions or pure compounds. It is important, therefore, when embarking on a natural products screening program, to coordinate bioassay capabilities to isolation protocols, in addition to other target selection criteria. The targets described below are of great contemporary relevance to human health concerns and each feature robust bioassay methodologies that assist in early crude extract level prioritization.

The ESKAPE Pathogens

With growing antibiotic resistance, and a decrease in antibiotic drug discovery, the Infectious Disease Society of America issued a 'call to arms' in 2009 to the drug discovery community to combat what they called the ESKAPE pathogens: the gram positive *Enterococcus faecium* and *Staphylococcus aureus*, and gram negative *Klebsiella pneumoniae, Acinetobacter baumannii, Pseudomonas aeruginosa*, and *Enterobacter cloacae*. (Boucher, H. W.; Talbot, G. H.; Bradley, J. S.; Edwards, J. E.; Gilbert, D.; Rice, L. B.; Scheld, M.; Spellberg, B.; Bartlett, J. Bad Bugs, No Drugs: No ESKAPE! An Update from the Infectious Diseases Society of America. *Clin. Infect. Dis.* 2009, 48 (1), 1-12). These clinically relevant, highly drug resistant pathogens represent a continuously growing threat to human health and an important target for drug discovery efforts. (Pogue, J. M.; Kaye, K. S.; Cohen, D. A.; Marchaim, D. Appropriate Antimicrobial Therapy in the Era of Multidrug-Resistant Human Pathogens. *Clin. Microbiol. Infect.* 2015, 21 (4), 302-312; Fleeman, R.; Lavoi, T. M.; Santos, R. G.; Morales, A.; Nefzi, A.; Welmaker, G. S.; Medina-Franco, J. L.; Giulianotti, M. A.; Houghten, R. A.; Shaw, L. N. Combinatorial Libraries as a Tool for the Discovery of Novel, Broad-Spectrum Antibacterial Agents Targeting the ESKAPE Pathogens. *J. Med. Chem.* 2015, 58 (8), 3340-3355).

*Leishmania donovani*

Cutaneous Leishmaniasis accounts for one million cases annually with 310 million people being at risk for contraction. Visceral Leishmaniasis accounts for 300,000 cases annually which result in 20,000 deaths annually. A neglected tropical disease (NTD), Leishmaniasis is a parasitic infection caused by an intramacrophage protozoa that is transmitted to humans by the bite of infected sandflies. The visceral form of this disease, most commonly caused by *Leishmania donovani*, is typically fatal when left untreated. Upon entering the host, the parasite—in a non-flagellated amastigote life stage—invades macrophage cells to travel through the body and reproduce. (Pulvertaft, R.; Hoyle, G. Stages in the Life-Cycyle of *Leishmania donovani*. *Trans R Soc Trop Med Hyg* 1960, 54, 191-196). Recent advances in infected macrophage in-vitro culture techniques allow for more clinically relevant assays to be performed in a high throughput screening (HTS) context. (Annang, F.; Perez-Moreno, G.; Garcia-Hernandez, R.; Cordon-Obras, C.; Martin, J.; Tormo, J. R.; Rodriguez, L.; de Pedro, N.; Gomez-Perez, V.; Valente, M.; Reyes, F.; Genilloud, O.; Vicente, F.; Castanys, S.; Ruiz-Perez, L. M.; Navarro, M.; Gamarro, F.; Gonzalez-Pacanowska, D. High-Throughput Screening Platform for Natural Product-Based Drug Discovery against 3 Neglected Tropical Diseases: Human African Trypanosomiasis, Leishmaniasis, and Chagas Disease. *J. Biomol. Screen.* 2015, 20 (1), 82-91; De Rycker, M.; Hallyburton, I.; Thomas, J.; Campbell, L.; Wyllie, S.; Joshi, D.; Cameron, S.; Gilbert, I. H.; Wyatt, P. G.; Frearson, J. A.; Fairlamb, A. H.; Gray, D. W. Comparison of a High-Throughput High-Content Intracellular *Leishmania donovani* Assay with an Axenic Amastigote Assay. *Antimicrob. Agents Chemother.* 2013, 57 (7), 2913-2922; Siqueira-Neto, J. L.; Moon, S.; Jang, J.; Yang, G.; Lee, C.; Moon, H. K.; Chatelain, E.; Genovesio, A.; Cechetto, J.; Freitas-Junior, L. H. An Image-Based High-Content Screening Assay for Compounds Targeting Intracellular *Leishmania donovani* Amastigotes in Human Macrophages. *PLoS Negl. Trop. Dis.* 2012, 6 (6)). These advancements will hopefully aid in the discovery of new treatments for this disease in the face of increasing resistance to existing treatments. (Balasegaram, M.; Ritmeijer, K.; Lima, M. A.; Burza, S.; Ortiz Genovese, G.; Milani, B.; Gaspani, S.; Potet, J.; Chappuis, F. Liposomal Amphotericin B as a Treatment for Human Leishmaniasis. *Expert Opin. Emerg. Drugs* 2012, 17 (4), 493-510).

*Mycobacterium tuberculosis*

Tuberculosis (TB) remains a global health crisis, despite the advances of the whole genome sequencing project that revealed the genome of *Mycobacterium tuberculosis*. This disease, whose latent form is estimated to infect one third of the world's population, poses many drug development hurdles. Multi-drug resistant (MDR-TB) and extensively drug resistant (XDRTB) strains have emerged despite the current course of treatment typically involving combinatorial therapies aimed directly at preventing resistance. Drug discovery efforts, therefore, must address new mechanisms of action or *M. tuberculosis* targets. Additionally, TB drugs have the burden of needing to be compatible in combinatorial treatments for the immunocompromised, particularly those with HIV/AIDS, among whom incidence of this disease are highest. (Lechartier, B.; Rybniker, J.; Zumla, A.; Cole, S. T. Tuberculosis Drug Discovery in the Post-Post-Genomic Era. *EMBO Mol. Med.* 2014, 6 (2), 1-11). Natural products based drug discovery against this target have revealed promising results, with many existing treatments coming from natural products. With such a demanding target comes the need to screen a broad swath of chemical space, confirming natural products drug discovery efforts as a promising way forward in the search for treatments of this disease. (Mdluli, K.; Kaneko, T.; Upton, A. The Tuberculosis Drug Discovery and Development Pipeline and Emerging Drug Targets. *Cold Spring Harb Perspect Med* 2015, 5).

*Clostridium difficile*

The leading cause of healthcare related infection, *Clostridium difficile* is an easily spread, diarrhea causing bacteria that is considered a threat to human health worldwide. The use of antibiotics which upset the human gut microbiome is the primary cause of *C. difficile* infection (CDI), but any immunocompromised individuals are at risk. With increasing incidences of resistance, recurrence, and mortality, the need for discovery of new treatments against this bacteria is imperative. Most challengingly, new drugs to fight CDI must act without impact on the normal human gut fauna. Many novel treatment avenues have been suggested, among which, the discovery and use of bacterial natural products remain of high interest. (Zucca, M.; Scutera, S.; Savoia, D. Novel Avenues for *Clostridium difficile* Infection Drug Discovery. *Expert Opin. Drug Discov.* 2013, 8 (4), 459-477; Suwantarat, N.; Bobak, D. A. Current Status of Nonantibiotic and Adjunct Therapies for *Clostridium difficile* Infection. *Curr. Infect. Dis. Rep.* 2011, 13 (1), 21-27; Spigaglia, P. Recent Advances in the Understanding of Antibiotic Resistance in *Clostridium difficile* Infection. *Ther. Adv. Infect. Dis.* 2016, 3 (1), 23-42).

*Naegleria fowleri*

*Naegleria fowleri* is a free living, warm-water loving amoeba that causes the nearly always fatal primary amoebic meningoencephalitis (PAM). Diagnosis of PAM is extremely difficult, and current treatment options are time sensitive and limited to existing drug combinations (e.g. Amphotericin B, fluconazole, and miltefosine). (Capewell, L. G.; Harris, A. M.; Yoder, J. S.; Cope, J. R.; Eddy, B. A.; Roy, S. L.; Visvesvara, G. S.; Fox, L. M.; Beach, M. J. Diagnosis, Clinical Course, and Treatment of Primary Amoebic Meningoencephalitis in the United States, 1937-2013; YODER, J. S.; EDDY, B. A.; VISVESVARA, G. S.; CAPEWELL, L.; BEACH, M. J. The Epidemiology of Primary Amoebic Meningoencephalitis in the USA, 1962-2008. *Epidemiol. Infect.* 2010, 138 (7), 968-975). As clinicians start to understand and diagnose PAM better, and the risk of this disease continues to rise with increasing global temperatures, new drugs that specifically target this amoeba are urgently needed.

Cancer Targets

With structures as diverse as their targets, natural products have long played a role in the treatment of various cancers. (Newman, D. J.; Cragg, G. M. Natural Products as Sources of New Drugs from 1981 to 2014. *J. Nat. Prod.* 2016, 79 (3), 629-661; Wani, M. C.; Taylor, H. L.; Wall, M. E.; Coggon, P.; McPhail, A. T. Plant Antitumor Agents. VI. Isolation and Structure of Taxol, a Novel Antileukemic and Antitumor Agent from *Taxus brevifolia*. *J. Am. Chem. Soc.* 1971, 93 (9), 2325-2327; Fenical, W.; Jensen, P.; Kauffman, C.; Mayhead, S.; Faulkner, D.; Sincich, C.; Rao, M.; Kantorowski, E.; West, L.; Strangman, W.; Shimizu, Y.; Li, B.; Thammana, S.; Drainville, K.; Davies-Coleman, M.; Kramer, R.; Fairchild, C.; Rose, W.; Wild, R.; Vite, G.; Peterson, R. New Anticancer Drugs from Cultured and Collected Marine Organisms. *Pharm. Biol.* 2003, 41 (sup1), 6-14). As understanding of the complex physiology of human cells (both healthy and cancerous) continues to grow, assays directed at testing compounds against highly specific cellular targets continue to emerge. Rather than whole cancer-cell assays, these target specific assays can help to exclude compounds that are broadly cytotoxic to all cells in favor of compounds that are active within the specific mechanism of action that is desired. Autopalmitoylation dysregulation is implicated in many disease states. In a newly developed assay, palmitoylation of proteins can be monitored for modulation by compounds of interest in a HTS manner. This allows compounds to be rapidly screened not for their effect on the whole cell, but rather just on this particular pathway of interest. (Hamel, L. D.; Deschenes, R. J.; Mitchell, D. A. A Fluorescence-Based Assay to Monitor Autopalmitoylation of zDHHC Proteins Applicable to High-Throughput Screening Q. *Anal. Biochem.* 2014, 460, 1-8).

SUMMARY OF INVENTION

Fungi are known to produce a wide range of secondary metabolites of interest in drug discovery efforts. In a search for new, bioactive natural products via a fungal metabolite screening program, five new compounds (1-5) were isolated. Bioactivities of the new compounds against various drug targets make these compounds and their derivatives of interest for further drug discovery efforts.

The present invention relates to compounds according to the structure:

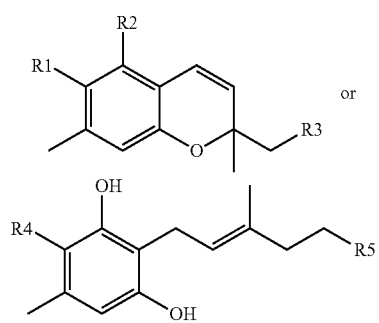

or where R1 can be

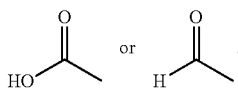

where R2 is a hydroxyl group.
where R3 can be

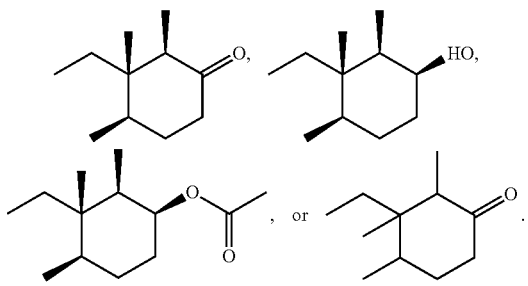

where R4 can be

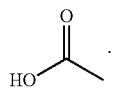

where R5 is

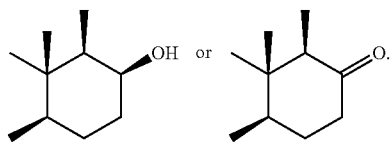

BRIEF DESCRIPTION OF THE DRAWINGS

For a fuller understanding of the invention, reference should be made to the following detailed description, taken in connection with the accompanying drawings, in which:

FIG. 12 is an image depicting important COSY and HMBC correlations in phomopsichromin E (5).

FIG. 13A-B is a series of images depicting a) Representative pie chart from bioassay data, in this case, ESKAPE activity, that shows the activity boosting effects of the epigenetic modification; b) Representative pie chart from bioassay data, in this case, ESKAPE activity, that demonstrates distribution of activity across the three treatment conditions. This is the overall trend amongst all testing completed to date.

DETAILED DESCRIPTION OF THE PREFERRED EMBODIMENT

Figure 1:
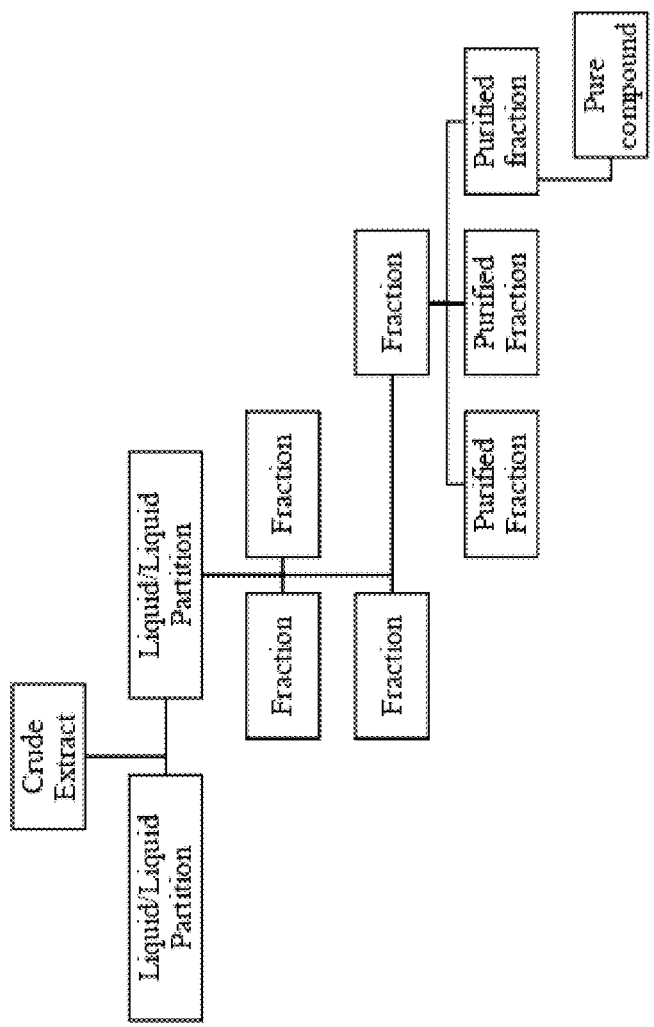
FIG. 1 is an image depicting a flowchart for natural product isolation.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The term "about" as used herein refers to being within an acceptable error range for the particular value as determined by one of ordinary skill in the art, which will depend in part on how the value is measured or determined, i.e. the limitations of the measurement system, i.e. the degree of precision required for a particular purpose. In general, the term "about" refers to being approximately or nearly and in the context of a numerical value or range set forth means±15% of the numerical value.

As used in the specification and claims, the singular form "a", "an" and "the" include plural references unless the context clearly dictates otherwise.

Compounds described herein can contain one or more double bonds and, thus, potentially give rise to cis/trans (E/Z) isomers, as well as other conformational isomers. Unless stated to the contrary, the invention includes all such possible isomers, as well as mixtures of isomers.

Unless stated to the contrary, a formula with chemical bonds shown only as solid lines and not as wedges or dashed lines contemplates each possible isomer, e.g. each enantiomer and diastereomer, and a mixture of isomers, such as racemic or scalemic mixture. Compounds described herein can contain one or more asymmetric centers and, thus potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

"Terpene" as used herein refers to organic hydrocarbons built up from isoprene, a hydrocarbon consisting of five carbon atoms attached to eight hydrogen atoms ($C_5H_8$). Terpenes have a general formula of $(C_5H_8)n$. "Terpenoids" refers to oxygenated derivatives of these hydrocarbons.

New Antimicrobials

Chemistry for terpenoid metabolites can be found in Ellestad, G. A. et al, 1969, herein incorporated by reference into this disclosure in its entirety (Ellestad, G. A., et al., Some new terpenoid metabolites from an unidentified *fusarium* species, Tetrahedron, 1969, 25(6): 1323-1334). Sesquiterpene hydroquinones and isolation thereof can be found in Shen et al. 2001, herein incorporated by reference by its entirety. (Shen, Y. C., et al., New sesquiterpene hydroquinones from a Taiwanese marine sponge *Hippospongia metachromia*, 2001, *J. Nat. Prod.*, 64:801-803).

BB11-2 Isolation

Small colonies of the fresh water bryozoan *Pectinatella magnifica* were noticed in a retention pond located in north Tampa, Fla. These colonial organisms were collected for chemical analysis. While collecting, one of the colonies was found to be growing around the end of a tree branch that was partially submerged in the water. A small piece of this branch was collected along with the bryozoan and returned to the lab for processing. Once in the lab, the branch was processed for microbial isolation as discussed herein.

From two SDA plates, 7 fungal isolates were obtained based on morphological features. These organisms were given a name of "BB11" and archived. Following chemical investigation of isolate BB11-2, fungal identification was obtained via Sanger sequencing of the 18S ribosomal spacer region. Forward primers for the 18S region are as follows: 5' NNNNNNNNNNNNNTTGGTTTCTAGGACCGCCG-TAATGATTAATAGGGACAG TCGGGGGCATCAGTAT-TCAATCGTCAGAG 3' (SEQ ID NO:1); 5' GTGAAAT-TCTTGGATCGATTGAAGACTAACTACTGCGAAAG ATTTGCCAA GGATGTTTTCATTAATCAGGAAC-GAAAGT 3' (SEQ ID NO:2); 5' TAGGGGATCGAAAAC-GATCAGATACCGTTGTAGTCTTAATCATAAACTATG CCCACTAGGGATCNGGCGGTGTTATTTCT 3' (SEQ ID NO:3). Reverse primers are as follows: 5' NNNNNNNNNNNNNNNCNGNTCNCCCCTTGTGGT-GCCCTTCCGT CAATTTCTTTAAGTTTCAGCCTTGC-GACCATACTCCC 3' (SEQ ID NO:4); 5' CCCAGAAC-CCAAAAACTTTACTTTCGTGTAAGGTGCCGAGC GGGTCAAGAA ATAACACCGCCCGATCCCTAGTCG-GCATA 3' (SEQ ID NO:5); 5' GTTTATGGTTAAGACTA-CAACGGTATCTGATCGTTTTCGATNCCCTAACTTT CGTTCCTGATTNANGANAACATCCTTGG 3' (SEQ ID NO:6); 5' GAAATGCTTTCCNANTAATNNGNCTTC-NATCAAATCCTCA 3' (SEQ ID NO:7). An NCBI nucleotide BLAST search returned identification as *Diaporthe* or *Phomopsis* sp.; genera that have been determined to be the same but represent different life cycles of these common, chemically rich endophytic fungi. (Gomes, R. R.; Glienke, C.; Videira, S. I. R.; Lombard, L.; Groenewald, J. Z.; Crous, P. W. *Diaporthe*: A Genus of Endophytic, Saprobic and Plant Pathogenic Fungi. *Persoonia Mol. Phylogeny Evol. Fungi* 2013, 31, 1-41; Dai, J.; Krohn, K.; Florke, U.; Gehle, D.; Aust, H. J.; Draeger, S.; Schulz, B.; Rheinheimer, J. Novel Highly Substituted Biraryl Ethers, Phomosines D-G, Isolated from the Endophytic Fungus *Phomopsis* Sp. from Adenocarpus Foliolosus. *European J. Org. Chem.* 2005, 4 (23), 5100-5105; Kobayashi, H.; Meguro, S.; Yoshimoto, T.; Namikoshi, M. Absolute Structure, Biosynthesis, and Anti-Microtubule Activity of Phomopsidin, Isolated from a Marine-Derived Fungus *Phomopsis* Sp. *Tetrahedron* 2003, 59 (4), 455-459; Isaka, M.; Jaturapat, A.; Rukseree, K.; Danwisetkanjana, K.; Tanticharoen, M.; Thebtaranonth, Y. Phomoxanthones A and B, Novel Xanthone Dimers from the Endophytic Fungus *Phomopsis* Species. *J. Nat. Prod.* 2001, 64 (8), 1015-1018; Tang, J. W.; Wang, W. G.; Li, A.; Yan, B. C.; Chen, R.; Li, X. N.; Du, X.; Sun, H. D.; Pu, J. X. Polyketides from the Endophytic Fungus *Phomopsis* Sp. sh917 by Using the One Strain/many Compounds Strategy. *Tetrahedron* 2016, 10, 2-9; Lin, X.; Huang, Y.; Fang, M.; Wang, J.; Zheng, Z.; Su, W. Cytotoxic and Antimicrobial Metabolites from Marine Lignicolous Fungi, *Diaporthe* Sp. *FEMS Microbiol. Lett.* 2005, 251 (1), 53-58; Dettrakul, S.; Kittakoop, P.; Isaka, M.; Nopichai, S.; Suyarnsestakorn, C.; Tanticharoen, M.; Thebtaranonth, Y. Antimycobacterial Pimarane Diterpenes from the Fungus *Diaporthe* Sp. *Bioorganic Med. Chem. Lett.* 2003, 13 (7), 1253-1255). The isolate is referred to herein as *Phomopsis* sp.

Initial Bioactivities and Scale-Up

Figure 2:
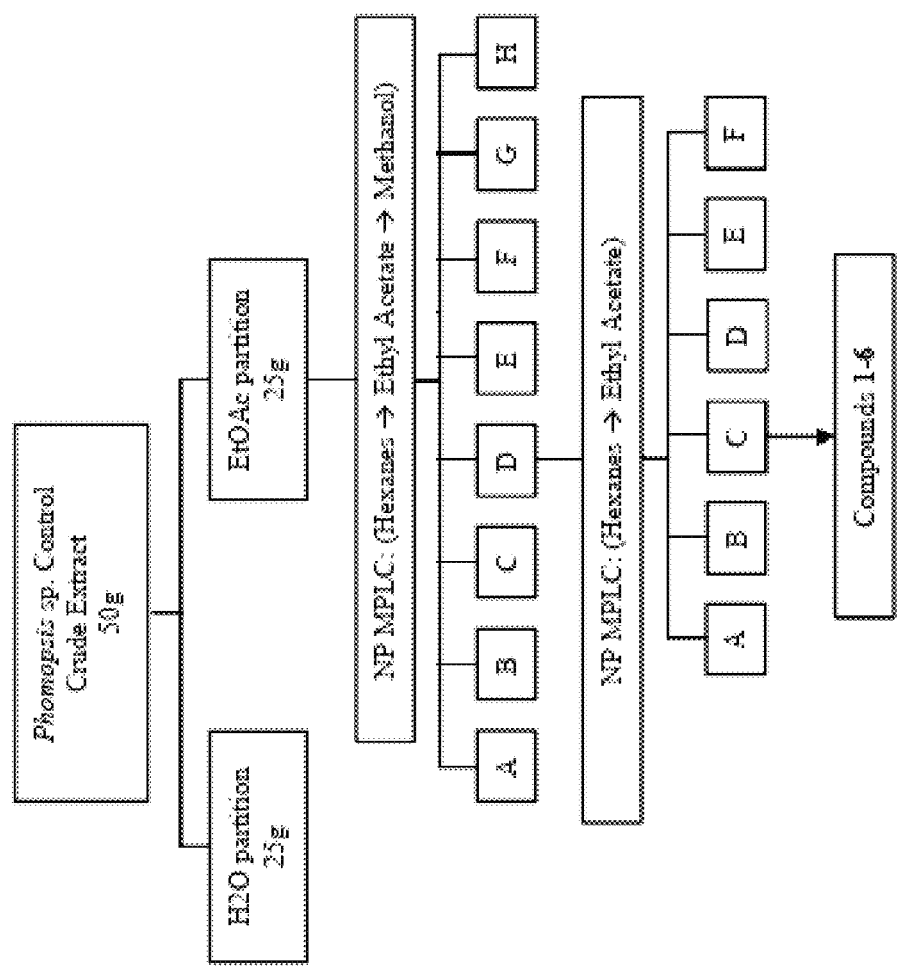
FIG. 2 is an image depicting an extraction scheme for *Phomopsis* sp. Control.

The BB11 fungal isolates were screened in a number of assays and assay development protocols and their extracts were known within the lab to be highly active with low cytotoxicity. Isolate BB11-2 was chosen for its reproducible bioactivity and tolerance towards multiple media types. As a part of a scale-up optimization study, BB11-2 was scaled up on rice media in three growth conditions: control (700 g of rice media+100 mL SDB), HDACi (700 g of rice media+a 435 µM solution of sodium butyrate in 100 mL SDB), and DNMTi (700 g of rice media+a 435 µM solution of 5-azacytidine in 100 mL SDB). After 21 days of growth, each extract was extracted in 1:3 MeOH/EtOAc solution overnight, followed by 2 subsequent 24 hour extractions in 100% EtOAc. The extracts for each of the three culture conditions were dried down and subjected to a H2O:EtOAc partition. The lipophilic partitions were each separated on NP MPLC (FIG. 2). The fractions of the control extract were further investigated.

Compound Isolation and Structure Elucidation

Figure 3:
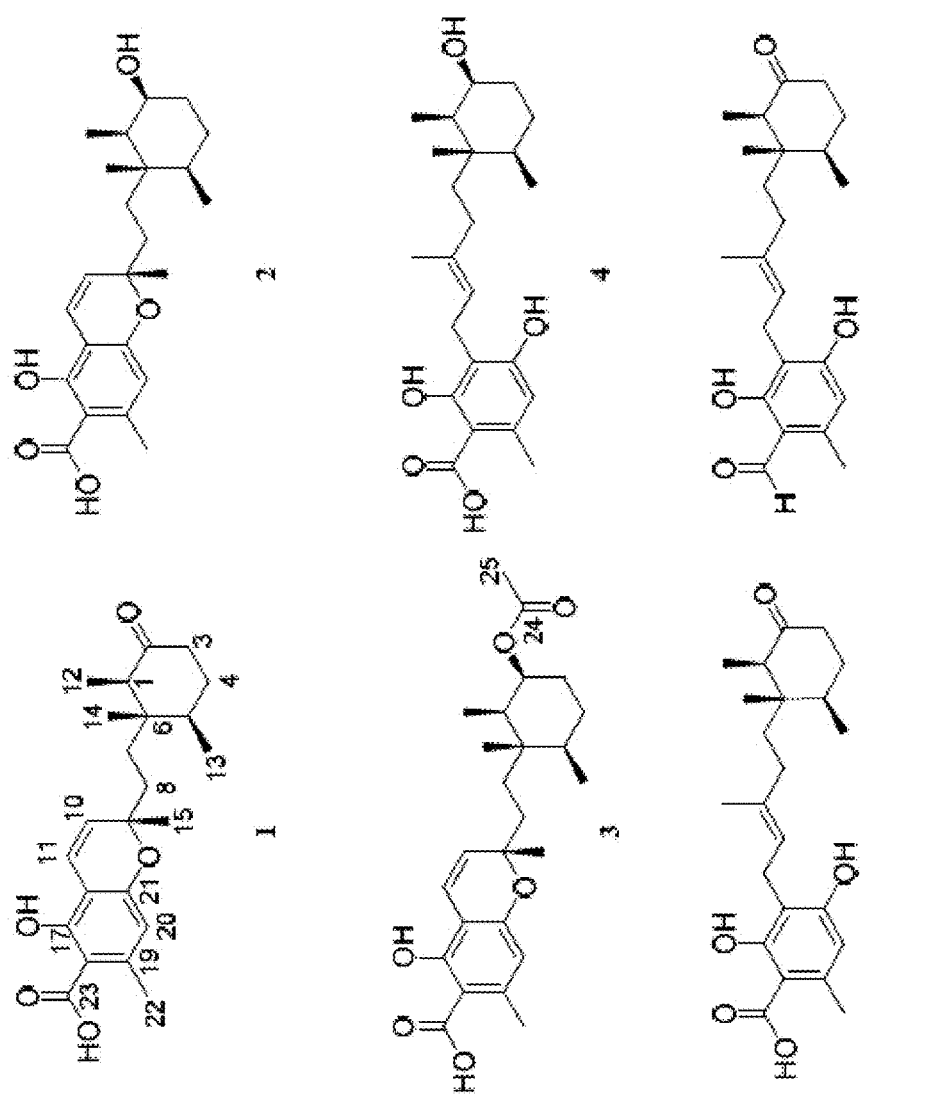
FIG. 3 is an image depicting chemical structures of new compounds 1-5 and known compound 6.

The extract of the control culture condition of *Phomopsis* sp. was investigated by NMR and bioactivity guided fractionation (FIG. 2) and yielded 5 new meroterpenes: phomopsichromins A-E (1-5), and the known compound LL-Z1272c (6) (FIG. 3). (Ellestad, G. A.; Evans, R. H.; Kunstmann, M. P. Some New Terpenoid Metabolites from an Unidentified *Fusarium* Species. *Tetrahedron* 1969, 25 (6), 1323-1334).

In the first MPLC separation of the lipophilic partition of the Control extract, the majority of the mass eluted in one large peak in approximately 1:1 n-hexanes:ethyl acetate. This fraction (Fraction D) was further purified via NP MPLC on an extended non-polar gradient (n-hexanes to ethyl acetate). Again, the majority of the mass eluted in a single peak in approximately 1:1 nhexanes:ethyl acetate (Fraction C). Further purification was accomplished on NP HPLC using a cyano column (CN capping of the silica particles) and UV detection. Compounds 1-6 (FIG. 3) were isolated as illustrated in FIG. 2.

Compounds 1-6 all share a sesquiterpene backbone functionalized differentially at C-9. 1-3 share a chromene substructure while compounds 4-6 feature a ring-opened subunit. The structures of Phomopsichromins A-E (1-5) were elucidated as described below.

Phomopsichromin A (1)

Figure 5:
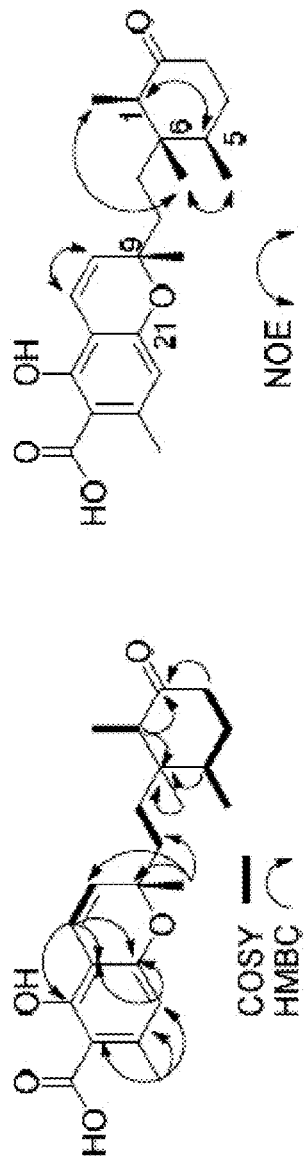
FIG. 5 is an image depicting important COSY, HMBC, and NOE correlations in phomopsichromin A (1).

Phomopsichromin A (1), $[\alpha]^{20}$D +1.2, was isolated as a white powder. The 1H NMR spectrum of 1 (Table 1) notably displayed 3 olefinic protons, peaks for 5 methyl substituents, and a phenol. The 13C NMR spectrum indicated the presence of a carboxylic acid ($\delta$C 175.18) and ketone ($\delta$C 213.87). Remaining 13 C signals were split between the aromatic and alkene regions and implied a high level of substitution on the aromatic ring (as evidenced by the small number of olefinic protons in the 1H NMR spectrum). The chromene substructure was tentatively assigned based on 2D NMR experiments and 13 C ppm shifts of carbons 9 and 21. The remaining terpene scaffold was completed based on HMBC and COSY NMR data (FIG. 5). HRESIMS of 1 (m/z 387.2137 [M+H]+) resembled compounds in the literature but did not match any exactly, confirming that 1 was a new compound. (Ellestad, G. A.; Evans, R. H.; Kunstmann, M. P. Some New Terpenoid Metabolites from an Unidentified *Fusarium* Species. *Tetrahedron* 1969, 25 (6), 1323-1334; Singh, S. B.; Zink, D. L.; Bills, G. F.; Jenkins, R. G.; Silverman, K. C.; Lingham, R. B. Cylindrol A: A Novel Inhibitor of Ras Farnesyl-Protein Transferase from Cylindrocarpon Lucidum. *Tetrahedron Lett.* 1995, 36 (28), 4935-4938; Singh, S. B.; Ball, R. G.; Bills, G. F.; Cascales, C.; Gibbs, J. B.; Goetz, M. A.; Hoogsteen, K.; Jenkins, R. G.; Liesch, J. M.; Lingham, R. B.; Silverman, K. C.; Zink, D. L. Chemistry and Biology of Cylindrols: Novel Inhibitors of Ras Farnesyl-Protein Transferase from Cylindrocarpon Lucidum. *J. Org. Chem.* 1996, 61 (22), 7727-7737; Ishibashi, M.; Ohizumi, Y.; Cheng, J.; Nakamura, H.; Sasaki, T.; Kobayashi, J. Metachromins A and B, Novel Antineoplastic Sesquiterpenoids from the Okinawan Sponge *Hippospongia* Cf. Metachromia. *J. Org. Chem.* 1988, 53 (12), 2855-2858; Takahashi, Y.; Yamada, M.; Kubota, T.; Fromont, J.; Kobayashi, J. Metachromins R-T, New Sesquiterpenoids from Marine Sponge Spongia Sp. *Chem. Pharm. Bull. (Tokyo).* 2007, 55 (12), 1731-1733).

TABLE 1

1D and 2D data for phomopsichromin A (1) in CDCl3.

| Pos | $\delta_C{}^b$ | $\delta_H$ (m, J(Hz))$^a$ | HMBC$^c$ |
|---|---|---|---|
| 1 | 50.4 | 2.41 (q, 6.6 × 2, 1 H) | 2, 5, 6, 7, 12, 14 |
| 2 | 213.8 | | |
| 3 | 41.5 | 2.33 (m, 1 H) | 2, 4, 5 |
| | | 2.36 (m, 1 H) | |
| 4 | 30.8 | 1.64 (m, 1 H) | 3, 5, 6, 13 |
| | | 1.85 (m, 1 H) | 2, 3, 5, 6 |
| 5 | 36.1 | 1.97 (m, 1 H) | 1, 3, 4, 6, 13 |
| 6 | 43.2 | | |
| 7 | 30.6 | 1.41 (m, 1 H) | 1, 5, 6, 8, 14 |
| | | 1.48 (m, 1 H) | 1, 5, 6, 8, 14 |
| 8 | 34.3 | 1.52 (m, 1 H) | 7, 9, 10 |
| | | 1.77 (m, 1 H) | 7, 15, 9, 10 |
| 9 | 79.89 | | |
| 10 | 125.8 | 5.46 (d, 10.2, 1 H) | 8, 9, 15, 16, 21 |
| 11 | 116.9 | 6.76 (d, 10.2, 1 H) | 9, 15, 16, 17, 21 |
| 12 | 7.5 | 0.91 (d, 6.8, 3 H) | 1, 2, 6 |
| 13 | 14.9 | 0.89 (d, 6.8, 3 H) | 4, 5, 6 |
| 14 | 15.4 | 0.59 (s, 3 H) | 1, 5, 6, 7 |
| 15 | 27 | 1.44 (s, 3 H) | 8, 9, 10, 11 |
| 16 | 106.8 | | |
| 17 | 160.6 | | |
| -OH | | 11.74 (s, 1 H) | 16, 17, 18, 21 |
| 18 | 103.6 | | |
| 19 | 144.4 | | |
| 20 | 111.9 | 6.24 (s, 1 H) | 10, 11, 16, 18, 21, 22, 23 |
| 21 | 158.6 | | |
| 22 | 24 | 2.55 (s, 3 H) | 17, 18, 19, 20, 21, 23 |
| 23 | 175.1 | | |

$^a$1H NMR recorded at 500 MHz reported in ppm (multiplicity, J-coupling in Hz, integration);
$^b$13C NMR recorded at 125 MHz;
$^c$recorded from a gHMBCAD experiment at 500 MHz and reported as positions of carbons Compound data for Phomopsichromin A (1) is as follows: $C_{23}H_{30}O_5$; HRESIMS m/z 369.2034 [M+H–H2O]+ ($C_{23}H_{29}O_4$ calculated, 369.2066), m/z 387.2137 [M+H]+ ($C_{23}H_{31}O_5$ calculated, 387.2171), m/z 409.1954 [M+Na]+ ($C_{23}H_{30}O_5Na$ calculated, 409.1991); UV (MeOH) λmax (log ε) 250 (4.97) nm; $[\alpha]^{20}{}_D$ +1.2 (c 0.1, MeOH); IR (thin film) 3450, 2980, 2360, 1700, 1600, 1575, 1450, 1400, 1300, 1090 cm$^{-1}$; 1H NMR Data (500 MHz, CDCl3) δ ppm 0.59 (s, 3H), 0.89 (d, J=6.8 Hz, 3H), 0.91 (d, J=6.8 Hz, 3H), 1.41 (m, 1H), 1.44 (s, 3H), 1.48 (m, 1H), 1.52 (m, 1H), 1.64 (m, 1H), 1.77 (m, 1H), 1.85 (m, 1H), 1.97 (m, 1H), 2.33 (m, 1H), 2.36 (m, 1H), 2.41 (q, J=6.6 Hz, 1H), 2.55 (s, 3H), 5.46 (d, J=10.2 Hz, 1H), 6.24 (s, 1H), 6.76 (d, J=10.2 Hz, 1H), 11.74 (s, 1H); 13C NMR (125 MHz, CDCl3) δ ppm 7.5 (CH3, C-12), 14.9 (CH3, C-13), 15.4 (CH3, C-14), 30.6 (CH2, C-7), 30.8 (CH2, C-4), 34.3 (CH2, C-8), 36.1 (CH, C-5), 41.5 (CH2, C-3), 43.2 (C-6), 50.4 (CH, C-1), 79.8 (C-9), 103.6 (C-18), 106.8 (C-16), 111.9 (CH, C-20), 116.9 (CH, C-11), 125.8 (CH, C-10), 144.4 (C-19), 158.6 (C-21), 160.6 (C-17), 175.1 (C-23) 213.8 (C-2).

Using the NMR data from these related compounds, the chromene substructure was confirmed. Relative stereochemical assignments at methyl-bearing carbons 1 (R), 5

(R), 6 (S), and 9 (S) were assigned via 1 and 2D NOE experiments (FIG. 5) and comparison to the literature. (Ishibashi, M.; Ohizumi, Y.; Cheng, J.; Nakamura, H.; Sasaki, T.; Kobayashi, J. Metachromins A and B, Novel Antineoplastic Sesquiterpenoids from the Okinawan Sponge *Hippospongia* Cf. *Metachromia*. *J. Org. Chem.* 1988, 53 (12), 2855-2858; Takahashi, Y.; Yamada, M.; Kubota, T.; Fromont, J.; Kobayashi, J. Metachromins R-T, New Sesquiterpenoids from Marine Sponge Spongia Sp. *Chem. Pharm. Bull.* (*Tokyo*). 2007, 55 (12), 1731-1733; Tanabe, M.; Suzuki, K. Detection of C—C Bond Fission during the Biosynthesis of the Fungal Triprenylphenol Ascochlorin Using [1,2-13C]-Acetate. *J.C.S. Chem. Comm.* 1974, No. 1, 445-446). ECD will be used to confirm absolute stereochemistry.

Phomopsichromin B (2)

Figure 6:
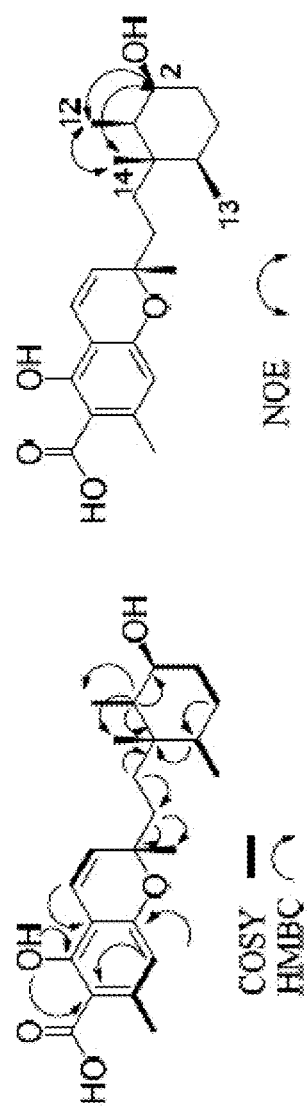
FIG. 6 is an image depicting important COSY, HMBC, and NOE correlations in phomopsichromin B (2).

Phomopsichromin B (2) was isolated as a white powder, C23H32O5, HRESIMS m/z 389.2322 [M+H]+ (calculated, 389.2283), $[\alpha]^{20}$D −1.5. Comparison to the HRMS of 1 indicated a difference of 2 protons. The appearance of a broad multiplet at δH 3.85 and the loss of the ketone signal at δC 213.87 inferred a reduction at C-2. The 2D NMR spectra further supported this assignment (FIG. 6). The stereochemistry at position 2 was determined to be S based on the multiplicity observed in the proton NMR spectrum. The observed J-values of the quartet at δH 3.85 most closely matched those expected from the axial orientation of the hydroxyl group.

TABLE 2

1D and 2D data for phomopsichromin B (2) in CDCl$_3$.

| Pos | $\delta_C{}^b$ | $\delta_H$ (m, J(Hz))$^a$ | HMBC$^c$ |
|---|---|---|---|
| 1 | 39.4 | 1.43 (m, 1H) | 2, 6, 12, 14 |
| 2 | 73.1 | 3.85 (q, 2.8, 1 H) | 3, 4, 6, 12 |
| 3 | 33.9 | 1.55 (m, 1 H) | 1, 5 |
|   |   | 1.8 (m, 1 H) | 1, 2, 4, 5 |
| 4 | 25.4 | 1.27 (m, 1 H) |   |
|   |   | 1.63 (m, 1 H) | 3, 5 |
| 5 | 36.5 | 1.46 (m, 1 H) | 6, 7, 14 |
| 6 | 38.2 |   |   |
| 7 | 30.9 | 1.35 (m, 2 H) | 5, 6, 8, 14 |
| 8 | 34.4 | 1.45 (m, 1 H) | 6, 7, 9 |
|   |   | 1.63 (m, 1 H) | 6, 7, 9, 10, 15 |
| 9 | 80.1 |   |   |
| 10 | 126.2 | 5.46 (d, 10.2, 1 H) | 8, 9, 15, 16 |
| 11 | 116.6 | 6.74 (d, 10.2, 1 H) | 9, 16, 17, 21 |
| 12 | 12.3 | 0.95 (d, 7.1, 3 H) | 1, 2, 6 |
| 13 | 15.6 | 0.82 (d, 6.6, 3 H) | 4, 5, 6 |
| 14 | 17.3 | 0.86 (s, 3H) | 7, 6, 5 |
| 15 | 27.1 | 1.41 (s, 3 H) | 8, 9, 10 |
| 16 | 106.9 |   |   |
| 17 | 160.6 |   |   |
| -OH |   | 11.80 (s, 1 H) | 16, 17, 18 |
| 18 | 103.4 |   |   |
| 19 | 144.1 |   |   |
| 20 | 111.9 | 6.22 (s, 1 H) | 16, 18, 21, 22 |
| 21 | 158.7 |   |   |
| 22 | 24.4 | 2.53 (s, 3 H) | 18, 19, 20 |
| 23 | 174.7 |   |   |

$^a$ $^1$H NMR recorded at 600 MHz, reported in ppm (multiplicity, J-coupling in Hz, integration);
$^b$ $^{13}$C NMR recorded at 125 MHz;
$^c$ recorded from a gHMBCAD experiment at 500 MHz and reported. as positions of carbons.

This orientation could also be observed in other related compounds in the literature. (Bieber, L. W.; Messana, I.; Lins, S. C.; Da Silva Filho, A. A.; Chiappeta, A. A.; De Mello, J. F. Meroterpenioid Naphthoquinones from Cordia Corymbosa. *Phytochemistry* 1990, 29(6), 1955-1959). The remaining chiral centers were determined to be the same as in 1. Again, the stereochemistry is confirmed via ECD.

Figure 7:
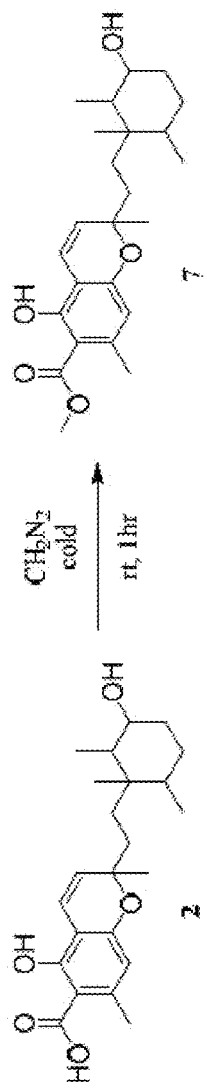
FIG. 7 is an image depicting methylation reaction of 2 to yield 7 with diazomethane.

Curiously, in multiple 1D NMR analyses of 2 over time, notable shifts in ppm were observed for some peaks (e.g. δH 6.22, 3.85, and 2.53; δC 73.17, 103.46, 158.73, and 174.72). The assumption was made that there were diastereoisomers present (further supported by some poorly resolved crystal data), however, various NP and RP HPLC attempts eluted a single peak in all conditions. The beginning, middle, and end of the peak were collected as separate fractions (a, b, and c) in an attempt to separate the diastereoisomers. Clear ppm differences were observed between fractions a and c, but they were chromatographically indistinguishable. The decision was made to methylate the carboxylic acid at C-23 in fractions a and c to reduce the effects of hydrogen bonding in separation attempts and aid in NMR spectral evaluation (FIG. 7).

The resulting methyl derivatives of fractions a and c (7) were confirmed by 1D NMR. All ppm differences between fractions a and c were lost, indicating that all previously noted shifts in ppm had been a concentration-based artifact of hydrogen bonding of 2 to itself in solution. 2 was determined to be a single diastereoisomer and remaining chemical and biological analyses were completed.

Compound data for Phomopsichromin B (2) is as follows: C23H32O5, HRMS m/z 371.2222 [M+H−H2O]±(C23H31O4 calculated, 371.2222), m/z 389.2322 [M+H]+ (C23H33O5 calculated, 389.2328), m/z 411.2145 [M+Na]+ (C23H32O5Na calculated, 411.2147); UV (MeOH) λmax (log ε) 250 (4.08) nm; $[\alpha]^{20}{}_D$ −1.5 (c 0.1, MeOH); IR (thin film) 3450, 2930, 2380, 1675, 1625, 1600, 1575, 1460, 1400, 1300, 1090 cm$^{-1}$; $^1$H NMR Data (600 MHz, CDCl$_3$) δ ppm 0.82 (d, J=6.6 Hz, 3H), 0.86 (s, 3H), 0.95 (d, J=7.1 Hz, 3H), 1.27 (m, 1H), 1.35 (m, 2H), 1.41 (s, 3H), 1.43 (m, 1H), 1.45 (m, 1H), 1.46 (m, 1H), 1.55 (m, 1H), 1.63 (m, 2H), 1.8 (m, 1H), 2.53 (s, 3H), 3.85 (q, 2.8, 1H), 5.46 (d, J=10.2 Hz, 1H), 6.22 (s, 1H), 6.74 (d, J=10.2 Hz, 1H), 11.80 (s, 1H); $^{13}$C NMR (125 MHz, CDCl$_3$) δ ppm 12.3 (CH$_3$, C-12), 15.6 (CH$_3$, C-13), 17.3 (CH$_3$, C-14), 24.4 (CH$_3$, C-22), 25.4 (CH$_2$, C-4), 27.0 (CH$_3$, C-15), 30.9 (CH$_2$, C-7), 33.9 (CH$_2$, C-3), 34.4 (CH$_2$, C-8), 36.5 (CH, C-5), 38.2 (C-6), 39.4 (CH, C-1), 73.1 (CH, C-2), 80.1 (C-9), 103.4 (C-18), 106.9 (C-16), 111.9 (CH, C-20), 116.6 (CH, C-11), 126.2 (CH, C-10), 144.1 (C-19), 158.7 (C-21), 160.6 (C-17), 174.7 (C-23).

Phomopsichromin C (3)

Figure 8:
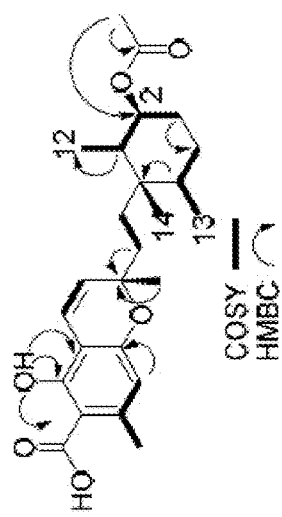
FIG. 8 is an image depicting important COSY, HMBC, and NOE correlations in phomopsichromin C (3).

Phomopsichromin C (3) was isolated as a white powder, $[\alpha]^{20}$D +1.3. 1H NMR data resembled 1 and 2 in the chromene region, however, the methyl signals at position 12, 13, and 14 were notably shifted downfield and were all overlapping (Table 3). New peaks at δC 170.87 and 21.4, with a new methyl signal in the 1H spectrum (δH 2.05) indicated added ester functionalization in the molecule. HRESIMS m/z 431.2434 [M+H]+ (calculated, 431.2389) gave a molecular formula of C25H34O6, confirming the addition of a —CO(O)CH3 group. The available 2D NMR data confirmed that the new functionalization was at C-2 (δC 75.16) (FIG. 8).

TABLE 3

1D and 2D data for phomopsichromin C (3) in CDCl$_3$.

| Pos | $\delta_C{}^b$ | $\delta_H$ (m, J(Hz))$^a$ | HMBC$^c$ |
|---|---|---|---|
| 1 | 38.5 | 1.55 (m, 1 H) | 6, 12, 14 |
| 2 | 75.1 | 4.97 (q, 2.0, 1 H) | 1 |
| 3 | 30.9 | 1.5 (m, 1 H) | 1, 2, 4, 5 |
|   |   | 1.81 (m, 1 H) |   |

TABLE 3-continued 1D and 2D data for phomopsichromin C (3) in CDCl$_3$.

| Pos | $\delta_C{}^b$ | $\delta_H$ (m, J(Hz))$^a$ | HMBC$^c$ |
|---|---|---|---|
| 4 | 25.8 | 1.29 (m, 1 H) | 2, 3, 5, 6, 13 |
|  |  | 1.5 (m, 1 H) |  |
| 5 | 36.2 | 1.47 (m, 1 H) | 3, 4, 6, 14 |
| 6 | 38.3 |  |  |
| 7 | 30.7 | 1.4 (m, 2 H) | 1, 5, 8, 9, 14 |
| 8 | 34.4 | 1.4 (m, 1 H) | 7, 9, 10, 11, 15 |
|  |  | 1.65 (m, 1 H) |  |
| 9 | 80.1 |  |  |
| 10 | 126.1 | 5.45 (d, 10.2, 1 H) | 8, 9, 15, 16, 21 |
| 11 | 116.7 | 6.74 (d, 10.0, 1 H) | 9, 15-17, 21 |
| 12 | 12.0 | 0.83 (m, 3 H) | 2 |
| 13 | 15.6 | 0.83 (m, 3 H) | 4 |
| 14 | 16.7 | 0.83 (m, 3 H) | 1, 5, 7, 8 |
| 15 | 27.1 | 1.4 (s, 3 H) | 8-11 |
| 16 | 106.8 |  |  |
| 17 | 160.6 |  |  |
| -OH |  | 11.82 (s, 1 H) | 16, 17, 18, 21 |
| 18 | 103.3 |  |  |
| 19 | 144.1 |  |  |
| 20 | 111.9 | 6.22 (s, 1 H) | 11, 16-18, 21-23 |
| 21 | 158.7 |  |  |
| 22 | 24.4 | 2.53 (s, 3 H) | 16-20, 23 |
| 23 | 174.4 |  |  |
| 24 | 170.8 |  |  |
| 25 | 21.4 | 2.05 (s, 3 H) | 2, 24 |

$^a$$^1$H NMR recorded at 600 MHz, reported in ppm (multiplicity, J-coupling in Hz, integration);
$^b$$^{13}$C NMR recorded at 125 MHz;
$^c$recorded from a gHMBCAD experiment at 500 MHz and reported as positions of carbons.

Figure 9:
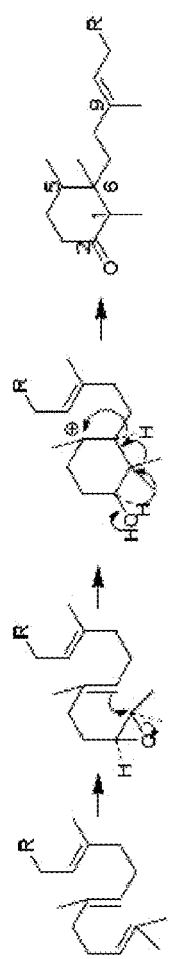
FIG. 9 is an image depicting the proposed biosynthetic pathway towards cyclohexane substructure of 1-6 from Tanabe and Suzuki, 1974.
Figure 10:
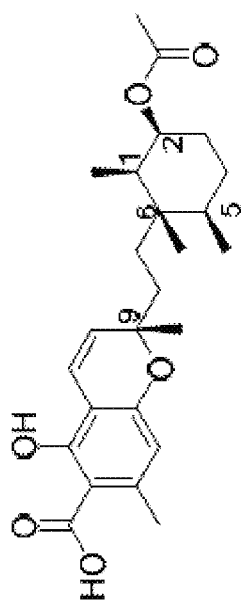
FIG. 10 is an image depicting proposed stereocenters in the cyclohexane ring of 3 sent for ECD calculations.

Due to the overlapping signals of the methyl signals on the cyclohexane ring of 3, elucidating the stereochemistry at C-1, 2, 5, and 6 based on NMR data posed a significant challenge. The methyl group at C-9 was assumed, as in compounds 1 and 2, to be S based on chemical shift. The stereochemistry at C-2 was again determined to be S based on the 1D 1H multiplicity. FIG. 9 illustrates the proposed biosynthetic pathway for the cyclohexane substructure of 1-5 based on work done by Tanabe and Suzuki in 1974 on a related compound. 13 This pathway indicates that the ketone at C-2 is a part of the precursor molecule, and therefore all reductions at C-2 occur post translationally. This suggests a conserved chirality at the centers at C-1, C-5, and C-6. Based on these assumptions, a compound with proposed stereochemistry (FIG. 10) was submitted for ECD.

Compound data for Phomopsichromin C (3): $C_{25}H_{34}O_6$; HRESIMS m/z 413.2330 [M+H−H$_2$O]$^+$ ($C_{25}H_{33}O_5$ calculated, 413.2328), m/z 431.2434 [M+H]$^+$ ($C_{25}H_{35}O_6$ calculated, 431.2434), m/z 453.2256 [M+Na]$^+$ ($C_{25}H_{34}O_6$Na calculated, 453.2253); UV (MeOH) λmax (log ε) 255 (4.21) nm; [α]$^{20}{}_D$ +1.3 (c 0.1, MeOH); IR (thin film) 2930, 1740, 1675, 1600, 1580, 1400, 1300, 1350, 1090 cm$^{-1}$; $^1$H NMR Data (600 MHz, CDCl$_3$) δ ppm 0.83 (2 d, J=6.6 Hz, 6H; s, 3H), 1.29 (m, 1H), 1.40-1.43 (m, 6H), 1.47 (m, 1H), 1.5 (m, 2H), 1.55 (m, 1H), 1.65 (m, 1H), 1.81 (m, 1H), 2.05 (s, 3H), 2.53 (s, 3H), 4.97 (q, 2.0, 1H), 5.45 (d, J=10.2 Hz, 1H), 6.22 (s, 1H), 6.74 (d, J=10.0 Hz, 1H), 11.82 (s, 1H); $^{13}$C NMR (125 MHz, CDCl$_3$) δ ppm 12.0 (CH$_3$, C-12), 15.6 (CH$_3$, C-13), 16.7 (CH$_3$, C-14), 21.4 (CH$_3$, C-25), 24.4 (CH$_3$, C-22), 25.8 (CH$_2$, C-4), 27.1 (CH$_3$, C-15), 30.7 (CH$_2$, C-7), 30.9 (CH$_2$, C-3), 34.4 (CH$_2$, C-8), 36.2 (CH, C-5), 38.3 (C, C-6), 38.5 (CH, C-1), 75.1.

Phomopsichromin D (4)

Figure 4:
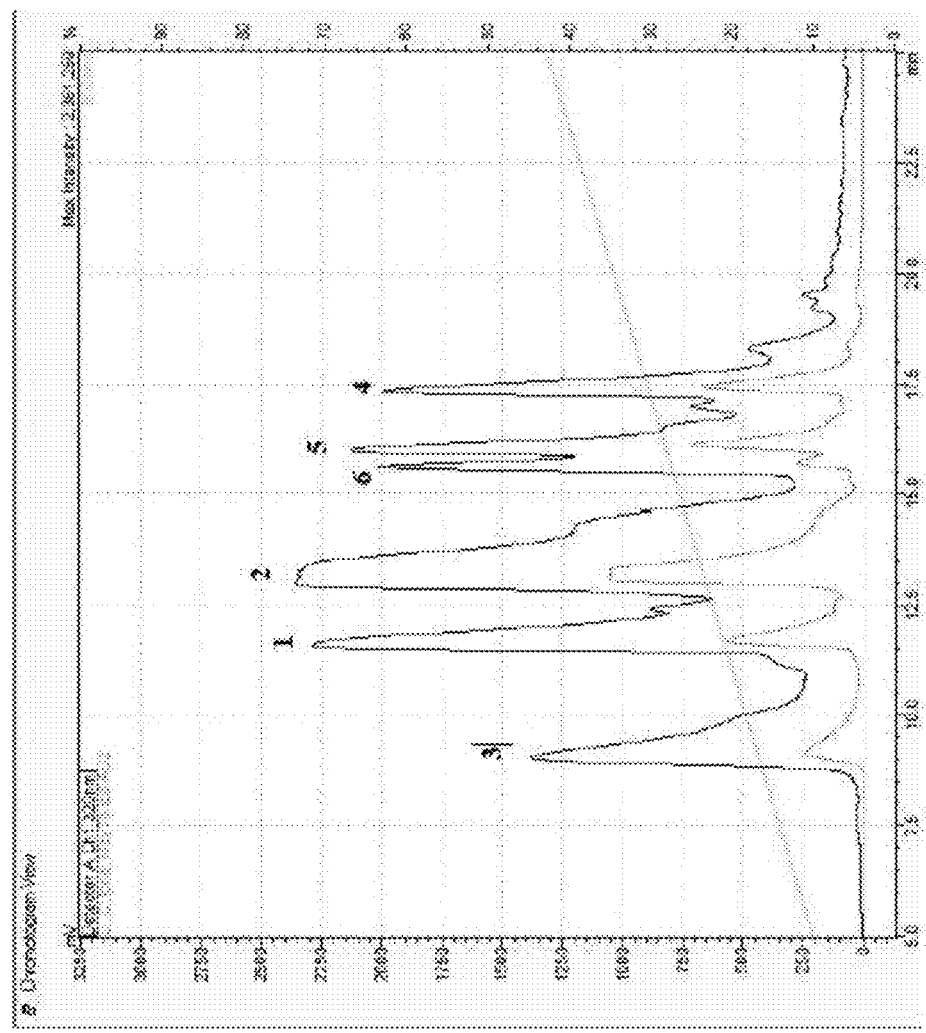
FIG. 4 is an image depicting NP HPLC chromatogram of fraction D_C (FIG. 2) from the control growth treatment of *Phomopsis* sp. Peaks are annotated with their isolated compounds (FIG. 3). Each compound required some further purification on reverse phase (RP) HPLC for structure elucidation and bioassay purposes, but represented the major component of each of the peaks seen. Black is the UV chromatogram at 320 nm, and blue is the ELSD trace.

Phomopsichromin D (4), C23H34O5, HRESIMS m/z 391.2473 [M+H]+ (calculated, 391.2440), [α]$^{20}$D +0.2) was isolated as a white powder from the last and least lipophilic HPLC fraction of MPLC fraction D_C (FIG. 4). 4 was notably distinct from 1-3 in that it was quite different in polarity (not soluble in CDCl3) and so all NMR data was obtained in DMSO-d6 (Table 4). The olefin region of the proton NMR spectrum of 4 was the most drastically different from compounds 1-3 and there was an additional phenol signal at δH 10.02, indicating that 4 lacked the completed chromene substructure.

TABLE 4

1D and 2D data for phomopsichromin D (4) in DMSO-d$_6$.

| Pos | $\delta_C{}^b$ | $\delta_H$ (m, J(Hz))$^a$ | HMBC$^c$ |
|---|---|---|---|
| 1 | 39.0 | 1.35 (m, 1 H) | 2, 5, 6, 12, 14 |
| 2 | 70.4 | 3.62 (q, 2.4, 1 H) | 4, 6, 12 |
| 3 | 34.1 | 1.4 (m, 1 H) | 4 |
|  |  | 1.6 (m, 1 H) | 4 |
| 4 | 25.5 | 1.13 (m, 1 H) | 1, 3, 5, 6, 14 |
|  |  | 1.53 (m, 1 H) |  |
| 5 | 36.0 | 1.4 (m, 1 H) | 4 |
| 6 | 38.0 |  |  |
| 7 | 36.0 | 1.17 (m, 1 H) | 1, 5, 6, 8, 9, 14 |
|  |  | 1.23 (m, 1 H) | 5, 6, 8, 9, 14 |
| 8 | 32.4 | 1.69 (m, 1 H) | 5, 15 |
|  |  | 1.75 (m, 1 H) | 5, 10, 11, 15 |
| 9 | 134.7 |  |  |
| 10 | 121.8 | 5.12 (br t, 6.9, 1 H) | 8, 11, 15, 16 |
| 11 | 21.5 | 3.16 (br d, 7.2, 2 H) | 7, 8, 9, 10, 15, 16, 17, 21 |
| 12 | 12.7 | 0.84 (d, 7.2, 3 H) | 1, 2, 6 |
| 13 | 15.7 | 0.74 (d, 6.6, 3 H) | 4 |
| 14 | 17.3 | 0.75 (s, 3 H) | 1, 6, 7 |
| 15 | 16.1 | 1.70 (s, 3 H) | 7, 8, 9, 10, 11, 16 |
| 16 | 112.0 |  |  |
| 17 | 159.6 |  |  |
| -OH |  | 12.61 (s, 1 H) | 16, 17, 18, 21 |
| 18 | 103.6 |  |  |
| 19 | 139.8 |  |  |
| 20 | 110.4 | 6.23 (s, 1 H) | 11, 16, 17, 18, 21, 22, 23 |
| 21 | 162.8 |  |  |
| -OH |  | 10.02 (s, 1 H) | 16, 17, 20, 21 |
| 22 | 23.8 | 2.38 (s, 3 H) | 18, 19, 20, 21, 23 |
| 23 | 174.1 |  |  |

$^a$$^1$H NMR recorded at 500 MHz, reported in ppm (multiplicity, J-coupling Hz integration);
$^b$$^{13}$C NMR recorded at 125 MHz;
$^c$recorded from a gHMBCAD experiment at 500 MHz and reported as positions of carbons.

Figure 11:
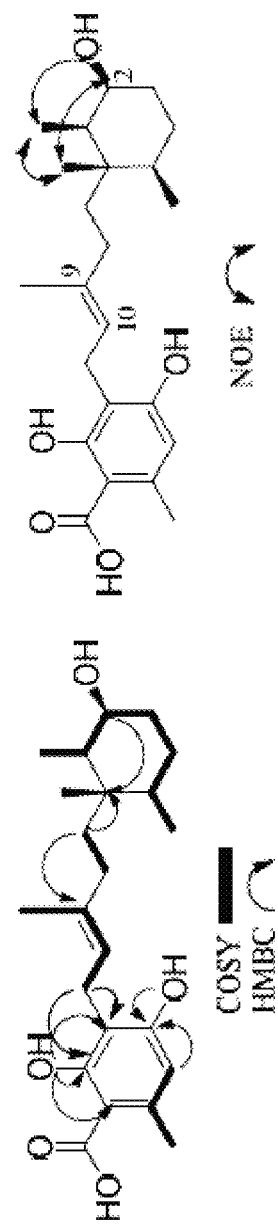
FIG. 11 is an image depicting important COSY, HMBC, and NOE correlations in phomopsichromin D (4).

2D NMR data (FIG. 11) further supported this, and the "open" carbon skeleton was assigned and confirmed by comparison to literature data on known compound 6. Stereochemistry on the cyclohexane ring was set as in compounds 1-3. The double bond of the open chain was determined to be E based on the comparison of the J-value of H-10 to the literature.

Compound data for Phomopsichromin D (4) is as follows: $C_{23}H_{34}O_5$; HRESIMS m/z 373.2373 [M+H−H$_2$O]$^+$ ($C_{23}H_{33}O_4$ calculated, 373.2379), m/z 391.2473 [M+H]$^+$ ($C_{23}H_{35}O_5$ calculated, 391.2484), m/z 413.2298 [M+Na]$^+$ ($C_{23}H_{34}O_5$Na calculated, 413.2304); UV (MeOH) λmax (log ε) 225 (5.89) nm; [α]$^{20}{}_D$ +0.2 (c 0.1, MeOH); IR (thin film) 3400, 2930, 1600, 1500, 1450, 1360, 1300, 1180, 1080 cm$^{-1}$; $^1$H NMR (500 MHz, DMSO-d$_6$) δ ppm 0.74 (d, J=6.6 Hz, 3H), 0.75 (s, 3H), 0.84 (d, J=7.1 Hz, 3H), 1.13 (m, 1H), 1.17 (m, 1H), 1.23 (m, 1H), 1.35 (m, 1H), 1.4 (m, 2H), 1.53 (m, 1H), 1.6 (m, 1H), 1.69 (m, 1H), 1.70 (s, 3H), 1.75 (m, 1H), 2.38 (s, 3H), 3.16 (br d, J=7.1 Hz, 2H), 3.62 (q, 2.4, 1H), 5.12 (br t, J=6.9 Hz, 1H), 6.23 (s, 1H), 10.02 (s, 1H), 12.61 (s, 1H); $^{13}$C NMR (125 MHz, DMSO-d$_6$) δ ppm 12.7 (CH$_3$, C-12), 15.7 (CH$_3$, C-13), 16.1 (CH$_3$, C-15), 17.3 (CH$_3$, C-14), 21.5 (CH$_2$, C-11), 23.8 (CH$_3$, C-22), 25.5 (CH$_2$, C-4), 32.4 (CH$_2$, C-8), 34.1 (CH$_2$, C-3), 36.0 (CH, C-5), 36.1 (CH, C-7), 38.0 (C, C-6), 39.0 (CH, C-1), 70.4 (CH, C-2), 103.6 (C, C-18), 110.4 (CH, C-20), 112.0 (C, C-16), 121.8 (CH, C-10), 134.7 (C, C-9), 139.8 (C, C-19), 159.6 (C, C-17), 162.8 (C, C-21), 174.1 (C, C-23).

Phomopsichromin E (5)

Phomopsichromin E (5) was isolated as a white powder, $C_{23}H_{32}O_5$; HRESIMS m/z 389.2363 [M+H]+, $[\alpha]^{20}D$ −0.4. By comparing 5 to 4 it was immediately evident that the only difference between the two was the increased oxidation at C-2. Comparison to 1 and 4, along with the 2D data for 5 (Table 5), completed the structure (FIG. 12).

TABLE 5

1D and 2D data for phomopsichromin E (5) in DMSO-$d_6$.

| Pos | $\delta_C{}^b$ | $\delta_H$ (m, J(Hz))$^a$ | HMBC$^c$ |
|---|---|---|---|
| 1 | 49.2 | 2.53 (q, 6.7, 1 H) | 2, 5, 6, 12, 14, |
| 2 | 212.6 | | |
| 3 | 40.7 | 2.1 (m, 1 H) | 1, 2, 4, 5 |
|   |      | 2.4 (m, 1 H) | |
| 4 | 30.3 | 1.47 (m, 1 H) | 3, 5, 13 |
|   |      | 1.76 (m, 1 H) | 6 |
| 5 | 35.0 | 1.99 (m, 1 H) | 3, 4, 6, 13, 4 |
| 6 | 42.7 | | |
| 7 | 35.4 | 1.23 (m, 1 H) | 5, 6, 8, 14 |
|   |      | 1.32 (m, 1 H) | 1, 6, 8, 9, 14 |
| 8 | 32.0 | 1.8 (m, 1 H) | 7, 9, 10, 15 |
|   |      | 1.91 (m, 1 H) | 7, 9, 10, 15 |
| 9 | 134.2 | | |
| 10 | 122.2 | 5.18 (br t, 6.8, 1 H) | 8, 11, 15, 16 |
| 11 | 21.5 | 3.17 (d, 7.1, 2 H) | 9, 10, 16, 17, 21 |
| 12 | 7.5 | 0.76 (d, 6.6, 3 H) | 1, 2, 6, 7 |
| 13 | 14.7 | 0.81 (d, 6.6, 3 H) | 4, 5, 6, 12 |
| 14 | 15.0 | 0.46 (s, 3 H) | 1, 5, 6 |
| 15 | 16.1 | 1.73 (s, 3 H) | 8, 9, 10, 16 |
| 16 | 111.9 | | |
| 17 | 159.6 | | |
| -OH |  | 12.62 (s, 1 H) | |
| 18 | 103.6 | | |
| 19 | 139.9 | | |
| 20 | 110.4 | 6.23 (s, 1 H) | 16, 17, 18, 22 |
| 21 | 162.8 | | |
| -OH |  | 10.04 (s, 1 H) | 16, 17, 20, 21 |
| 22 | 23.7 | 2.39 (s, 3 H) | 18, 19, 20 |
| 23 | 174.1 | | |

$^a$$^1$H NMR recorded at 500 MHz, reported in ppm (multiplicity J-coupling in Hz, integration);
$^b$$^{13}$C NMR recorded at 200 MHz;
$^c$recorded from a gHMBCAD experiment at 600 MHz and reported as positions of carbons.

Compound data for Phomopsichromin E (5) is as follows: $C_{23}H_{32}O_5$; HRESIMS m/z 371.2229 [M+H−H$_2$O]$^+$ ($C_{23}H_{31}O_4$ calculated 371.2222), 389.2363 [M+H]$^+$ ($C_{23}H_{33}O_5$ calculated 389.2328), 411.2152 [M+Na]$^+$ ($C_{23}H_{32}O_5$Na calculated 411.2147); UV (MeOH) λmax (log ε) 220 (4.14); $[\alpha]^{20}{}_D$ −0.4 (c 0.1, MeOH); IR (thin film) 3390, 2950, 1590, 1450, 1300, 1160, 1090, 1020 cm$^{-1}$; $^1$H NMR Data (600 MHz, DMSO-$d_6$) δ ppm 0.46 (s, 3H), 0.76 (d, J=6.6 Hz, 3H), 0.81 (d, J=6.6 Hz, 3H), 1.23 (m, 1H), 1.32 (m, 1H), 1.47 (m, 1H), 1.73 (s, 3H), 1.76 (m, 1H), 1.80 (m, 1H), 1.91 (m, 1H), 1.99 (s, 1 H), 2.10 (m, 1H), 2.39 (s, 3H), 2.40 (m, 1H), 2.53 (q, J=6.7 Hz, 1H), 3.17 (d, J=7.1 Hz, 2H), 5.18 (br t, J=6.7 Hz, 1H), 6.23 (s, 1H), 10.04 (s, 1H), 12.62 (s, 1H); $^{13}$C NMR (125 MHz, DMSO-$d_6$) δ ppm 7.5 (CH$_3$, C-12), 14.7 (CH$_3$, C-13), 15.0 (CH$_3$, C-14), 16.1 (CH$_3$, C-15), 21.5 (CH$_2$, C-11), 23.7 (CH$_3$, C-22), 30.3 (CH$_2$, C-4), 32.0 (CH$_2$, C-8), 35.0 (CH, C-5), 35.4 (CH$_2$, C-7), 40.7 (CH$_2$, C-3), 42.7 (C, C-6), 49.2 (CH, C-1), 103.6 (C, C-18), 110.4 (CH, C-20), 111.9 (C, C-16), 122.2 (CH, C-10), 134.2 (C, C-9), 139.9 (C, C-19), 159.6 (C, C-17), 162.8 (C, C-21), 174.1 (COOH, C-23), 212.6 (C, C-2).

Bioactivities

As shown in Table 6 below, Phomopsichromins A (1), B (2), C (3), and E (5) all show reasonable activity against the infected macrophage model of the *Leishmania donovani* parasite at 3, 1.9, 0.67, and 0.80 μM, respectively. Interestingly, neither phomopsichromin D (4) nor LL-Z1272ε (6) showed any activity towards the parasite or the macrophages.

Phomopsichromin C (3) was the only compound with any notable activity against any of the ESKAPE pathogens, with an MIC against MRSA of 58 μM. In a drug wash-out study, 3 was determined to be bactericidal. Impressively, this compound exhibits an MBC99 of 47 μM, which is reasonably close to the control gentamicin (20 μM in this assay). However, 3 also displays notable cytotoxicity towards HepG4 human liver cells, with an LD50 of 37 μM. Further supporting its cytotoxicity and lack of specificity, 3 is also active against the macrophage contained *Leishmania donovani* as mentioned above.

1, 2, and 5 all displayed activity against MRSA at extremely high concentrations (>500 μM) and further cytotoxicity testing may be useful. If these compounds continue to be selective against the *Leishmania donovani* parasite, further biological testing against that, and other parasite targets would be warranted.

TABLE 6

Pure compound bioactivities of 1-6.

| | Pure Compound Bioactivities | | |
|---|---|---|---|
| Compound | MRSA IC$_{50}$ (μM) | *L. donovani* IC$_{50}$ (μM) | Other |
| 1 | 518 | 3 | |
| 2 | 515 | 1.9 | |
| 3 | 58 | 0.67 | MRSA MBC$_{99}$: 47 μM |
| | | | HepG4 LD$_{50}$: 37 μM |
| 4 | NA | NA | |
| 5 | 515 | 0.80 | |
| 6 | NA | 13 | |

While none of the phomopsichromins immediately emerge as promising lead compounds against ESKAPE or *Leishmania donovani*, with a group of compounds of this size, an interesting "natural structure activity relationship (SAR) study" is beginning to take form. It is notable that 4 remains inactive, despite being nothing more than the ring-open form of 2. Meanwhile, 1 and its ring opened form, 5, display similar bioactivities. While six compounds are hardly enough to constitute a true SAR study, one can imagine that with the isolation (or synthesis) of more of these analogs, a pharmacophore may well begin to emerge. A fungal source is ideal for such studies as more material of these, and any other discovered compounds, could be obtained quite easily and in high quantities.

Materials and Methods

Microbial Isolation Protocols

Nutrient media components (SDB, PDB, TSA, Actinomycete Isolation Agar, Malt Extract Agar) and agar were produced by BD™ Difco™ and purchased through Fisher Scientific. Glycerol, nystatin, cycloheximide, and chloramphenicol were purchased from Sigma Aldrich®. Solid media was mixed, heated, and autoclaved according to manufacturer's instructions and poured to set in Fisherbrand™ petri dishes.

After collections, field plates were incubated at 20-25° C. (room temperature), 4° C. (refrigerated), or 26-30° C. (heated) as source organism or microbial targets dictated. Generally, bacterial plates were heated and fungal plates were left at room temperature for collections in warm climates. Cold water microbial isolation generally took place with refrigeration. Field plates were incubated for 1-4 weeks, and disposed of after all colonies were isolated and/or after the whole plate was covered in microbial growth. Isolated pure colonies were grown on SDA (fungi) and TSA (bacteria) for archiving as described above. Descriptions of each organism on this standard media were recorded.

Screening Protocols

Each fungal isolate was grown on SDA from either glycerol stocks or isolation plates, and after a colony was established, was subsampled for screening. 1 cm cubes of fungal material and agar were inoculated in triplicate into 3 sterile Eppendorf™ tubes containing 1.25 mL each: SDB (control), 100 µM sodium butyrate in SDB (HDACi), and 100 µM 5-aza-cytidine in SDB (DNMTi). Sodium butyrate and 5-aza-cytidine were purchased from Sigma Aldrich®. The SDB/modifier/fungal mixture was agitated, and then each poured over 1 g rice media in a Fisherbrand™ 20 mL glass scintillation vial. Rice media was made by autoclaving 1 g (¼ tsp) of brown rice with 4 mL DI water. Once inoculated, rice vials were incubated at 28° C. for 21 days. After 21 days, all contaminated/non-growing culture sets were removed. Cultures were spritzed with ~5000 µL distilled MeOH. The fungal rice cake was broken apart with a clean spatula. 10 mL distilled EtOAc was added using a glass 10 mL pipette and allow to extract overnight on bench top. Extracts were carefully decanted into clean, pre-weighed scintillation vials after 24 hours. Extracts were dried under air for 24 hours, resuspended in DMSO at a concentration of 10 mg/mL, and plated in 96-well format on a TECAN Freedom EVO 150 liquid handling automated workstation. Five replicate Corning™ clear polystyrene 96-well microplates were prepared with 150 µL of extracts/well for bioassay. Remaining extract material was stored in duplicate Fisherbrand™ 96-well DeepWell™ polypropylene microplates. All extract plates were stored at −20° C.

LC-QToF-MS Protocols

Extracts were dried of DMSO and suspended in MeOH at a concentration of 0.1 mg/mL. The resulting solution was filtered over 0.2 µm Phenomenex® RC syringe filters and were injected in triplicate on the LC-QToF-MS for analysis.

Analysis was completed on an Agilent 6540 LC/QTOF with Agilent Jet-stream Electrospray Ionization. A Kinetex C18 (5 µm, 100 Å, 2.1 mm ID, 50 mm length) column was used.

Metabolomic and Statistical Analysis Protocols

Each sample for metabolomics analysis was prepared as above and run in triplicate according to the run parameters above. Resulting chromatograms were subjected to processing by Agilent MassHunter Qualitative Analysis. First, a list of compounds was generated using the Find By Molecular Feature tool. A peak height cutoff was set at 100 counts and results were limited to the largest 5000 compounds. Results were exported to .cef files that were transferred to Agilent Mass Profiler Professional (MPP). In MPP replicates were averaged and blanks were subtracted. The resulting table of samples and chemical entities (mass @ retention time) was exported via Microsoft Excel and opened in Primer 6 for statistical analysis (Clarke, K. R.; Gorley, R. N. 2006. PRIMER v6: User Manual/Tutorial. Primer-E, Plymouth). Abundances were square root normalized and factors such as culture conditions and bioactivities were added to each sample identity. A Bray-Curtis similarity matrix was constructed from which cluster (dendogram) and multidimensional scaling (MDS) plots could be created.

Scale-Up Protocols

A scale-up protocol that mirrored the screening culture protocol was developed. The optimized procedure was enacted for all scale-up level screening. Rice media was prepared in a Type 3 T Unicorn bag according to the following procedure: 300 g of brown rice was mixed with 500 mL DI water and a heat sealer was used to seal the bag. Rice was autoclaved on a liquid cycle for 30 minutes at 121° C. Each hit organism chosen for scale-up was grown on SDA from either glycerol stocks or isolation plates, and after a colony was established, was subsampled for screening. 1 cm cubes of fungal material and agar were inoculated in triplicate into 3 sterile 50 mL Falcon™ tubes containing 50 mL each: SDB (control), 100 µM sodium butyrate in SDB (HDACi), and 100 µM 5-aza-cytidine in SDB (DNMTi). Rice bags were cut open in a sterile environment, the fungal/liquid media mixture poured in, and resealed. Rice was agitated once a week for a 21 day culture period. Extraction was completed by spritzing the culture with distilled MeOH to dampen the spores, transferring the material to a large beaker, and extracting overnight in a 1:3 MeOH:EtoAc mixture, followed by two 24-hour extractions in EtOAc. Extracts were collected, filtered, and dried down for chemical analysis.

Conclusion

The *Phomopsis* sp. isolate proved to be a producer of new, bioactive chemistry and may have biosynthetic potential remaining to be discovered. All six compounds discussed herein were isolated from the extract of the control growth condition. The extracts from the modified growth conditions remain to be explored. Additionally, NMR data suggests that there may be more phomopsichromins (or other known or new derivatives) as minor components of the investigated fractions that were abandoned due to time constraints. This strain remains archived in the lab fungal library, along with the other 6 isolates from the branch piece. These organisms are all known to produce bioactive extracts and would all be interesting targets for further chemical analysis and growth culture optimization.

This genera is known to have great biosynthetic potential and despite being such a well-studied organism, environmental strains such as the one investigated here continue to be producers of new compounds. Environmental microbial isolates are a promising source of new chemistry for drug discovery.

Fungal Library

General Protocol

Isolation techniques vary according to source and isolate targets, but can be described by the following general protocol: 1) tissue surface sterilization with a 10% bleach solution and/or isopropyl alcohol; 2) tissue subsampling into 1 cm cross-sections; 3) plating in triplicate onto solid media plates of variable composition; 4) careful monitoring of colony growth on solid media plates for a period of 1-4 weeks in the lab; and 5) transferring individual colonies to new isolation plates of similar composition. The last step is repeated until a pure colony is established for each isolate.

Variations in solid media plate composition are employed to target a wide range of fungi and bacteria, and all tissue samples collected are plated across 6-10 different media types to access the microbial diversity that can be found living within each target organism.[2] Each plate type is designed with the following general ingredients in varying concentrations: a nutrient source, agar, salt, and small molecule antibacterial and antifungal agents in sub-lethal doses to discourage the growth of fast-growing organisms. Available nutrient mixtures include: Sabaraud Dextrose Broth (SDB), Potato Dextrose Broth (PDB), Tryptic Soy Broth (TSB), Malt Broth, Actino Agar, and glycerol. Small molecule additives include: nystatin, cycloheximide, and chloramphenicol. Solid media types are curated for each collection expedition based on source and microbial targets.

Collection locations and source organisms represented in the isolate library are varied. Some examples of organisms commonly sampled for microbial isolation include: Floridian mangroves (*Rhizophora mangle, Avicennia germinans*, and *Laguncularia racemose*), mangrove associated trees (*Conocarpus erectus*, and *Coccoloba uvifera*), and benthic marine invertebrates including sponges, tunicates, and corals. Collection date, location, and source organism identification is all carefully recorded in field notebooks during each expedition.

To accommodate different field conditions, two different collection techniques have been developed. The first technique is field plating, in which tissue samples are surface sterilized and directly plated on location onto solid media plates ("field plates"), which are then transferred back to the lab for monitoring of growth. The second technique is glycerol cryotube preservation, in which tissue samples are surface sterilized, frozen and stored for transit in a 20% glycerol solution in cryotubes before being plated in the lab. This allows for microbial collections to take place around the world, preserving tissues and micro-organisms until they can be processed in the lab.

After establishing a pure isolate, all micro-organisms are archived in a 20% glycerol solution at −80° C. Bacterial cells are suspended in the solution, while fungal material is stored as small cubes of growth cut from SDA isolation plates. Isolates are identified according to the following nomenclature: "Collection Location, Year—Source Organism Number—Isolation Plate Type-Isolate Number". In this way, isolates can easily be grouped and retrieved according to any one of the collection or isolation parameters. Nearly 75% of the existing fungal isolates in this library were subjected to an epigenetics based high throughput screening (HTS) project.

An epigenetics based fungal screening program was designed and a culture miniaturization and modification protocol was developed to accommodate the use of 20 mL scintillation vials and a brown rice media. The histone deacetylase (HDAC) inhibitor sodium butyrate, and the DNA methyltransferase (DNMT) inhibitor 5-azacytidine were employed at concentrations of 100 μM for epigenetic modification. With a target of screening 500 organisms in 3 growth conditions (Control, HDACi, and DNMTi) each month for 12 months, goal-oriented timelines and protocols were developed and put in place.

The resulting extract library was dispersed for screening and archived in DMSO at a concentration of 10 mg/mL in 96-well plate format. Beyond the scope of the original two grant funded screening targets (the ESKAPE pathogens and *Leishmania donovani*), extracts have been distributed for screening in a number of additional targets, resulting in a body of data that can inform high level prioritization of active extracts. Additional screening is ongoing, but extract data to date includes bioactivities against the ESKAPE pathogens, *Leishmania donovani*, J774 macrophage cells, *Mycobacterium tuberculosis, Clostridium difficile*, and *Naegleria fowleri*. The library was additionally screened against a number of cell-based cancer targets and in a yeast based multiplex assay for anti-helminthics. Some active extracts were investigated by metabolomic analysis.

Metabolic Analysis

Extracts from a subset of organisms producing bioactivities were subjected to metabolomics analysis to investigate and confirm chemical diversity of the extract library and effectiveness of epigenetic modification techniques. Bioassay results showed desirable distribution of active extracts among the three culture conditions, and in each assay, organisms displaying activity only after modification accounted for 15-30% of all activity observed (FIG. 13).

To support and further investigate this diversity of activity, 123 extracts from 41 active organisms were analyzed via LC-QToF-MS. This subset of samples included active and non-active extracts (for instance, in the case that an organism only displayed activity after modification, the control extract was still included in the analysis). It included a wide range of isolates from different collections, isolation media, and source organisms. The LC-QToF-MS data were summarized into a list of 'chemical entities' (HRESIMS @ retention time) for each sample using Agilent Qualitative Analysis and Mass Profiler Professional software. Each sample, identified by its list of chemical entities, could then be statistically compared using Multidimensional Scaling (MDS). Each sample was also identified by a number of additional factors, including biological activity, culture treatment, and isolate identity. Using Primer 6 software, MDS plots were generated and annotated with any of these factors. This analysis allowed for a visual representation of the chemical similarity of the isolates and extracts to one another, and verified the chemical diversity of both the fungal library as well as the different culture treatments.

It was found that some organisms share less than 20% similarity with the other analyzed organisms (e.g. KML12-14MG-B2a). Additionally, for some organisms, different culture conditions induce an extract dissimilarity as high as 60% (e.g. EG10-47C-1). This data illustrates not only chemical uniqueness between different fungal isolates, validating the collection and isolation protocols, but also allows organisms in which the epigenetic modification has had a large impact on the metabolite profile to be identified. Organisms whose modified extracts exhibit unique chemistry and biological activities would be of high interest for scale up and chemical analysis. Through the processing for MDS analysis, this data is also ideally prepared for dereplication efforts. With a robustly annotated database of known cytotoxins, nuisance compounds could be quickly identified and their extracts de-prioritized. This data represents an exercise in metabolomics analysis of a small subset of screened extracts, but could be scaled up and performed on the entire extract library for high-level analysis of all available chemistry.

Training Set Results

Another subset of the extract library (1305 extracts, 13% of the total library) was screened fully against *Mycobacterium tuberculosis* (TB), the ESAKPE pathogens, *Leishmania donovani, Naegleria fowleri*, and the J774 murine macrophage cell line. Using stringent definitions of 'active' to moderate the hit rate, 16% of these 1305 extracts were determined to be active. While this number is quite large, this is a result of the fact that 77% of the hits were hits in only one assay. Within this subset, accounting for all bioactivities, the previously observed trends in each of the individual assays (FIG. 13) were verified; the three culture treatments were equally effective in producing active extracts, and 39% of active fungi only produced hits in the HDACi and DNMTi culture conditions.

Figure 14:
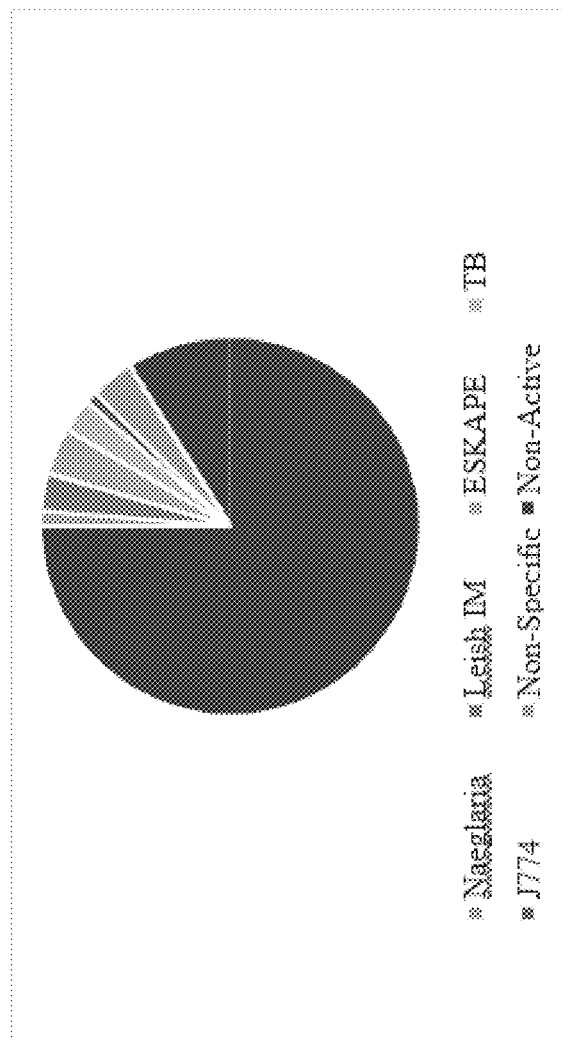
FIG. 14 is an image depicting selectivity of active extracts.

To analyze this data in the most meaningful way, strict activity cut-offs were set for each bioassay. For simplicity, the ESKAPE pathogens' MICs were reported as a single scaled score[4] for all 6 pathogens; an extract was considered 'active' in this assay if it had a scaled score ≥7. For highest clinical relevance, only extracts exhibiting an IC50 value <1 µg mL-1 in the infected macrophage model of the *Leishmania donovani* parasite were included. TB activity was included when ≥85%, and activity against *Naegleria fowleri* was defined as inhibition of >33% at either concentration tested (50 and 5 µg/mL). Any cytotoxicity against the J774 macrophage cells up to 20 µg/mL was also included. Results can be seen in FIG. 14.

Only 48 active extracts (23% of total active, 4% of total screened) were not specific to a single target organism. 17 extracts (8%, 1%) were active only against *N. fowleri*, 53 (25%, 4%) against the ESKAPE panel, 37 (17%, 3%) against *Mycobacterium tuberculosis*, 41 (20%, 3%) against the *L. donovani* infected macrophage, and 14 (7%, 1%) were cytotoxic only against the J774 macrophages. When the definition of 'active' was relaxed in a secondary hit, (i.e. an extract was only considered 'selective' if it had reported activity only one of the 4 assays) 100 extracts, 48% of active extracts, retained their qualification as 'selective'.

This is a unique set of data featuring extracts of diverse fungal origin screened against a wide range of eukaryotic and prokaryotic disease causing organisms. The specificity of bioactivity in this data set suggests unique underlying chemical profiles and, gratifyingly, provides strong support to the screening program design. With this data, the inventors have demonstrated that vigorous front-end investigation (multiple bioassays, metabolomic analyses, dereplication, etc.) of a library of extracts can inform scale-up prioritization in a highly effective way for the greatest chance of isolating new, bioactive natural products. Scale-up efforts are underway to further validate these methods.

With such promising data from the extract library, scale-ups of bioactive fungi have commenced. A scale-up protocol was developed and samples prioritized according to data available at the time. With the completed analysis of the training set, newly prioritized organisms have been identified and are available for chemical investigation in future. Extracts that feature specific, potent, and induced bioactivities can be scaled up and subjected to chemical analysis including new dereplication protocols as updated databases become available. With the plethora of front-end analysis that has been employed and presented here, organisms can now be chosen for chemical investigation with confidence in the chances of discovering new, bioactive secondary metabolites.

New Citreohybriddione

Citreohybridones and Citreohybriddiones

Figure 15:
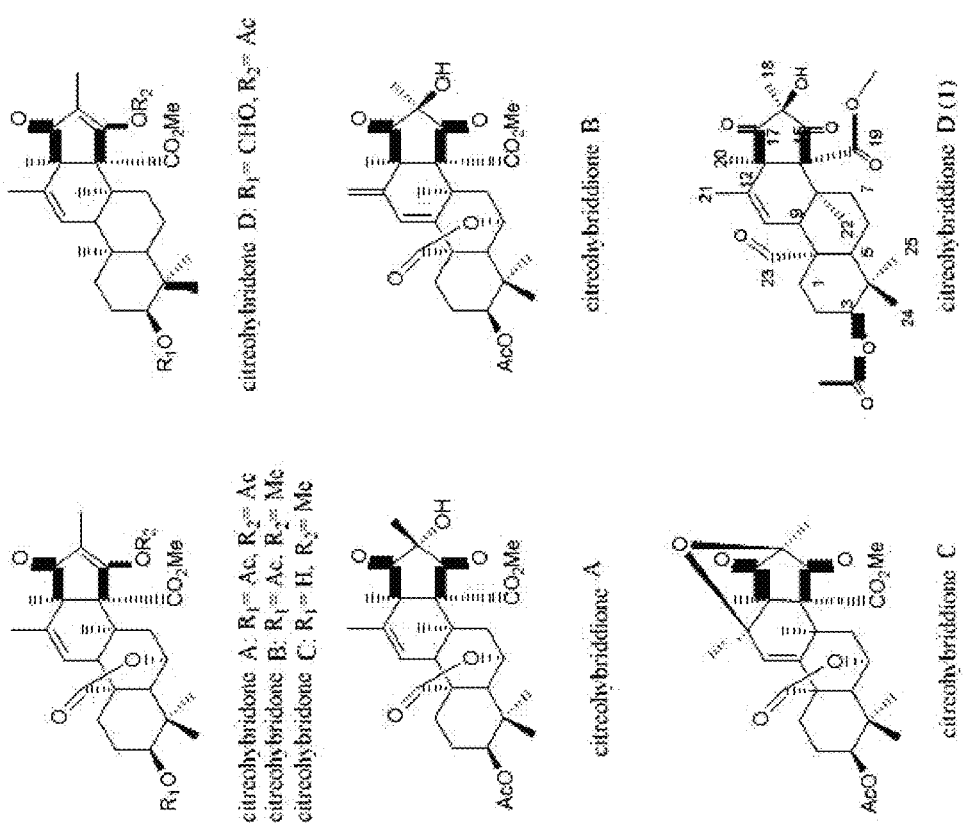
FIG. 15 is a series of images of previously reported citreohybridones, citreohybriddiones A-C, and the new citreohybriddione D (1).

The hybrid strain KO 0031 of *Penicillium citreo-viride* B. IFO 6200 and 4692 has been reported to be a prolific producer of meroterpenoid secondary metabolites. (Kosemura, S. Meroterpenoids from *Penicillium citreo-viride* B. IFO 4692 and 6200 Hybrid. *Tetrahedron* 2003, 59 (27), 5055-5072). Many of these hybrid polyketide-terpenoids are known to be feeding deterrents against the crop pest *Plutella xylostella*. (Kosemura, S.; Yamamura, S. Isolation and Biosynthetic Pathway for Citreohybridones from the Hybrid Strain KO 0031 Derived from *Penicillium* species. *Tetrahedron Lett.* 1997, 38 (35), 6221-6224; Kosemura, S.; Matsunaga, K.; Yamamura, S. Citreohybriddiones A and B and Related Terpenoids, New Metabolites of a Hybrid Strain KO 0031 Derived from *Penicillium citreo-viride* B. IFO 6200 and 4692. *Chem. Lett.* 1991, 1811-1814; Kosemura, S.; Matsou, S.; Yamamura, S. Citreohybriddione C, A Meroterpenoid of a Hybrid Strain KO 0031 Derived from *Penicillium citreo-viride* B. IFO 6200 and 4692. *Phytochemistry* 1996, 43 (6), 1231-1234; Kosemura, S.; Miyata, H.; Yamamura, S.; Albone, K.; Simpson, T. J. Biosynthetic Studies on Citreohybridones, Metabolites of a Hybrid Strain KO 0031 Derived from *Penicillium citreo-viride* B. IFO 6200 and 4692. *J. Chem. Soc. Perkin Trans* 1994, No. 1, 135-139). The previously reported citreohybridones and citreohybriddiones are two groups of these fungal natural products (FIG. 15). The inventors have isolated a new citreohybriddione (citreohybriddione D, 1) from an environmental *Penicillium* sp. fungus.

KML12-14MG-B2a Isolation

A number of collection trips to the Keys Marine Lab, Long Key, Fla. have targeted mangrove endophytes. Traveling by canoe and using field plating techniques, samples were collected from areas all around the facility targeting a broad range of micro-organisms. The Keys Marine Lab is uniquely located with access to a wide variety of mangrove environments.

KML12-14MG-B2a is a *Penicillium* sp. isolated from the 2012 Keys Marine Lab trip. This organism was isolated from the stem tissue of a juvenile *Rhizophora mangle* tree in an exposed mangrove community on the west side of Long Key. This fungus was isolated on a solid water agar plate containing sub-lethal doses of both nystatin and cycloheximide. On SDA this organism has a typical *Penicillium* morphology, growing radially from the inoculated mycelia with a light green/white color and fluffy sporulating bodies.

Initial Bioactivities, Scale-Up, Epigenetic Modification, and Identification

Similar to other fungal isolates in the microbial library, KML12-14MG-B2a was cultured and screened as a part of the screening program discussed above. This isolate emerged early as an important hit against the ESKAPE pathogens, hitting against both gram positive and gram negative pathogens in the Control and HDACi growth conditions (Table 7). In support of the design of the screening program, the HDACi culture produced a consistently active extract across replicate cultures, while repeated Control cultures produced inconsistent activity. Demonstrating the ability of these organisms to regulate their biosynthetic machinery and the effectiveness of the HDACi culture conditions, KML12-14MG-B2a became a model organism for scale-up and chemical investigation protocols.

TABLE 7

Screening results for KML12-14MG-B2a.

| Sample Information | | | MIC (µg/mL) | | | | |
| --- | --- | --- | --- | --- | --- | --- | --- |
| Date | Loc | Extract ID | 200 | 100 | 50 | 25 | 10 |
| Jan. 9, 2014 | F1 | KML12-14MG-B2a (HIT) CONTROL | EKAP | EKAP | EKAP | EAP | EA |
| Jan. 9, 2014 | F2 | KML12-14MG-B2a (HIT) HDAC | EKAP | EKAP | — | — | — |
| Jan. 9, 2014 | F3 | KML12-14MG-B2a (HIT) DNMT | — | — | — | — | — |
| Feb. 3, 2014 | P2 D7 | KML12-14MG-B2a (HIT) CONTROL | — | — | — | — | — |

TABLE 7-continued

Screening results for KML12-14MG-B2a.

| Sample Information | | | MIC (µg/mL) | | | | |
|---|---|---|---|---|---|---|---|
| Date | Loc | Extract ID | 200 | 100 | 50 | 25 | 10 |
| Feb. 3, 2014 | P2 D8 | KML12-14MG-B2a (HIT) HDAC | ESKAP | ESKAP | ESKAP | EKP | EK |
| Feb. 3, 2014 | P2 D9 | KML12-14MG-B2a (HIT) DNMT | — | — | — | — | — |

This organism was screened multiple times as a part of a subset of isolates chosen to verify reproducibility in the screening protocol. Activity is indicated by the first letter of the pathogen the extract showed activity against. E = *Enterococcus faecium*, S = *Staphylococcus aureus*, K = *Klebsiella pneumoniae*, A = *Acinetobacter baumannii*, P = *Pseudomonas aeruginosa*.

KML12-14MG-B2a was scaled up in control culture conditions on 700 g of brown rice (autoclaved with 1.4 L DI water) and inoculated in 100 mL of SDB in 2 types of Unicorn brand mycobags and a 3 L fernbach flask. After 21 days of incubation, both types of mycobag (Unicorn types 3 T and 14 A) were found to produce sterile, fully optimized growth (i.e. all rice material covered with growth) that resulted in extracts of similar mass. The fernbach flask culture proved significantly less desirable, with fungal growth only on the top of the solid rice due to an inability to agitate the culture throughout the culture process.

Epigenetically modified cultures on KML12-14MG-B2a were then scaled up using the same protocols (at this time, Unicorn bag types 3 T and 14 A were used interchangeably according to supply. Type 3 T bags were later purchased in bulk and all further scale-ups done in those bags). Again, resulting growth was uncontaminated and represented complete media coverage. The cultures each resulted in approximately 70 g of crude extract after a 3 day exhaustive extraction (day 1: 50 mL MeOH, 750 mL EtOAc; days 2 and 3: 800 mL EtOAc). Extracts were filtered over celite and sent for bioassay. Unfortunately, the crude extracts of the scale-ups did not replicate the activity seen in the small scale cultures. A liquid:liquid partition between EtOAc and $H_2O$, followed by NP MPLC separation of the EtOAc partition was performed on each extract, and the resulting fractions sent for bioassay. Again, disappointingly, the fractions returned inactive. Scale-up optimization efforts were continued with other organisms in search of a scale up protocol that could be standardized and used in a scale-up screening program. Due to interesting NMR data, chemical investigation continued on the fractions of the HDACi extract of KML12-14MG-B2a.

KML12-14MG-B2a was identified using sanger sequencing of the 18S ribosomal spacer region. Agreeing with the previously observed morphology, the isolate was identified to the genus level as a *Penicillium* sp.

Compound Isolation and Structure Elucidation

Figure 16:
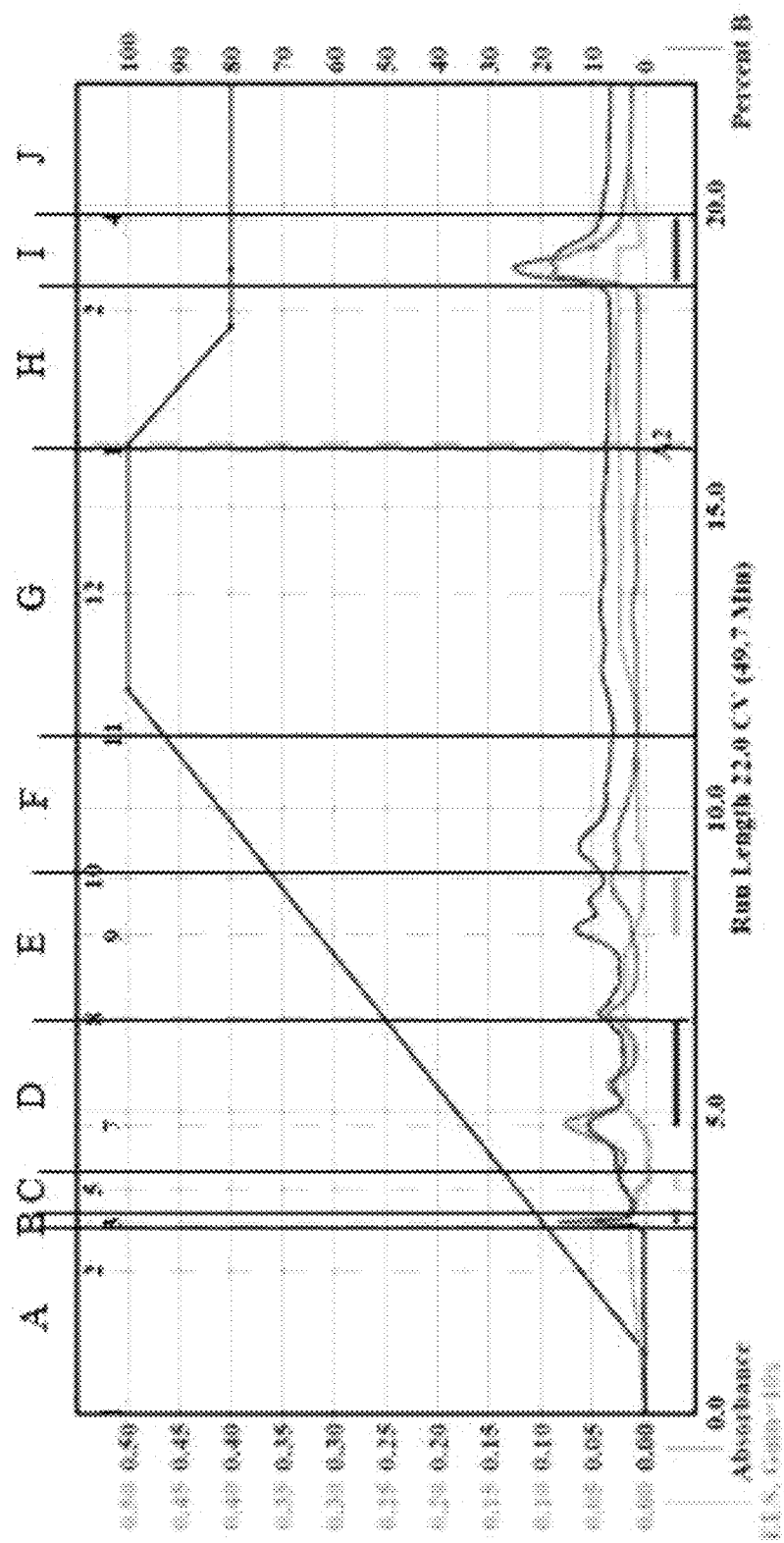
FIG. 16 is an image depicting the NP MPLC chromatogram of KML12-14MG-B2a HDACi.
Figure 17:
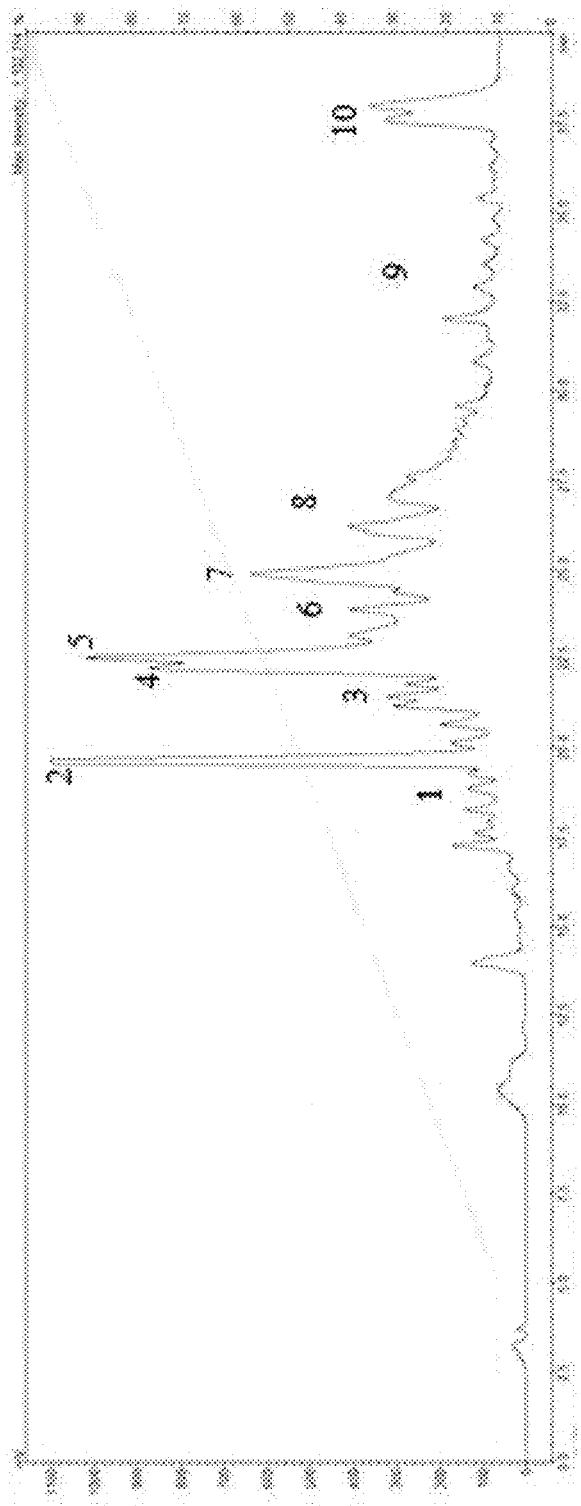
FIG. 17 is an image depicting the NP HPLC chromatogram of KML12-14MG-B2a HDACi-F.

The MPLC separation of KML12-14MG-B2a HDACi resulted in 10 fraction (FIG. 16). With no bioactivity in any of the fractions, compound elucidation proceeded via NMR guided fractionation. NMR analysis of all 10 fractions identified fraction F as interesting for further investigation. HPLC separation of F was completed in normal phase (n-hexanes:ethyl acetate) on a silica column to yield 10 fractions (FIG. 17). Fraction F-2 was discovered to contain the new meroterpenoid, citreohybriddione D (1).

Fraction F-2 was further purified on silica to yield compound 1. The $^1H$ NMR spectrum of 1 was notable in that it contained 8 methyl signals (Table 8) and almost nothing in the olefin region. Investigation of the $^{13}C$ data confirmed the presence of a large number of quaternary carbons, indicating a highly functionalized fused ring system such as a polyketide. The HRESIMS of 503.2640 $[M+H]^+$ resembled the terpenoid skeletons of the citreohybridones and citreohybriddiones, but did not match any of the previously reported compounds. $^{13}C$ NMR signals of carbons 1-12 strongly matched citreohybridone D, however carbons 13-18 more closely resembled citreohybriddione B.

TABLE 8

1D and 2D data for citreohybriddione D (1) in $CDCl_3$.

| Pos | $\delta_C{}^b$ | $\delta_H$ (m, J(Hz))$^a$ | HMBC$^c$ |
|---|---|---|---|
| 1 | 27.8 | 1.03 (m, 1 H) | 2, 9, 10, 22, 23, 25 |
|   |      | 2.38 (m, 1 H) | 3, 5, 9, 10 |
| 2 | 23.3 | 1.6 (m, 2 H) | 10 |
| 3 | 76.8 | 4.68 (t, 2.6, 1 H) | 1, 5, 26 |
| 4 | 36.9 | | |
| 5 | 47.7 | 1.83 (m, 1 H) | 4, 6, 10, 23, 24 |
| 6 | 16.9 | 1.8 (m, 1 H) | 4, 8, 10 |
|   |      | 2.01 (m, 1 H) | 7, 10 |
| 7 | 30.8 | 2.83 (m, 1 H) | 5, 6, 8, 22 |
|   |      | 2.38 (m, 1 H) | 5, 9, 10 |
| 8 | 38.6 | | 8, 10, 11, 12, 23 |
| 9 | 53.5 | 2.21 (m, 1 H) | |
| 10 | 52.2 | | |
| 11 | 126.4 | 5.85 (s, 1 H) | 8, 9, 10, 13, 21 |
| 12 | 133.0 | | |
| 13 | 60.8 | | |
| 14 | 70.4 | | |
| 15 | 210.6 | | |
| 16 | 72.1 | | |
| 17 | 206.7 | | |
| 18 | 19.8 | 1.4 (s, 3 H) | 15, 16, 17 |
| 19 | 167.3 | | |
| 20 | 16.4 | 1.31 (s, 3 H) | 12, 13, 14, 17 |
| 21 | 18.8 | 1.7 (s, 3 H) | 11, 12, 13 |
| 22 | 19.5 | 1.17 (s, 3 H) | 7, 8, 9, 14 |
| 23 | 204.4 | 10.14 (s, 1 H) | 1, 10, 22 |
| 24 | 26.5 | 0.97 (s, 3 H) | 2, 3, 4, 5, 25 |
| 25 | 21.3 | 0.9 (s, 3 H) | 3, 4, 5, 24 |
| 3-OAc | 170.6 | | |
| 3- OAc | 21.3 | 2.12 (s, 3 H) | 26 |
| 16- OH | | 2.16 (s, 1 H) | 15, 16, 17 |
| 19- OMe | 52.0 | 36.3 (s, 3 H) | 19 |

$^a$$^1H$ NMR recorded at 500 MHz, reported in ppm (multiplicity J-coupling in Hz, integration);
$^b$$^{13}C$ NMR recorded at 200 MHz;
$^c$recorded from a gHMBCAD experiment at 500 MHz and reported as positions of carbons.

Figure 18:
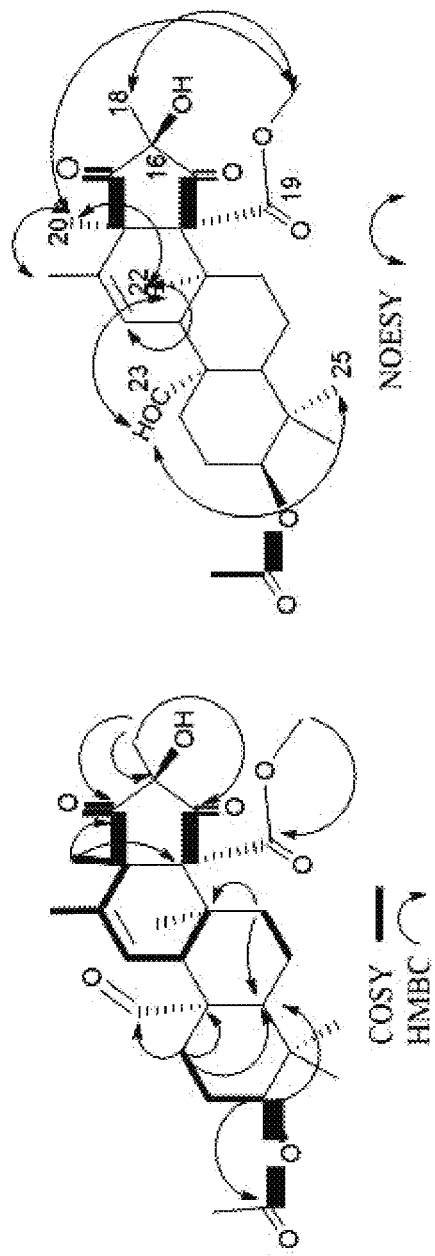
FIG. 18 is an image depicting important COSY, HMBC, and NOESY correlations in Citreohybriddione D (1).
Figure 19:
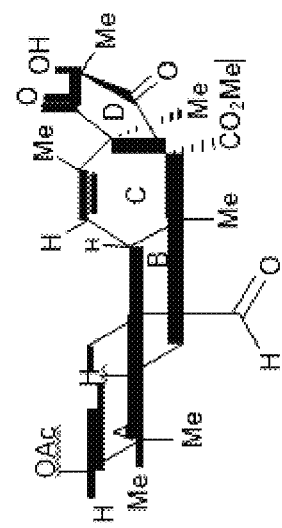
FIG. 19 is an image depicting a 3D depiction of 1 for stereochemical review.

With conformation from 2D NMR experiments (FIG. 18), it was determined that 1 is, in fact a new citreohybriddione lacking any lactone or epoxide ring structures. 2D NOESY data confirmed that the absolute stereochemistry matches what has been previously reported for similar compounds (FIG. 19). (Kosemura, S. Meroterpenoids from *Penicillium citreo-viride* B. IFO 4692 and 6200 Hybrid. *Tetrahedron* 2003, 59 (27), 5055-5072).

NOE correlations between the methoxy at C-19 ($\delta_H$ 3.63) and the methyl groups at C-18 ($\delta_H$ 1.40) and C-20 ($\delta_H$ 1.31) confirmed that the D-ring in 1 is up as in the other citreohybriddiones. The alcohol on C-16 of 1 has the same orientation as that in citreohybriddione B. Through-space correlations between C-22, 23, and 25 confirm that the stereochemistry of the A and B rings of 1 are as reported in citreohybriddione A.

Compound data for Citreohybriddione D (1) as follows: $C_{28}H_{38}O_8$; HRESIMS m/z 443.2431 [M–OAc]$^+$ ($C_{26}H_{35}O_6$ calculated, 443.2434), 503.2640 [M+H]$^+$ ($C_{28}H_{39}O_8$ calculated, 503.2645), 525.2465 [M+Na]$^+$ ($C_{28}H_{38}O_8$Na calculated, 525.2464); $[\alpha]^{20}_D$ +0.4 (c 0.1, MeOH); $^1$H NMR Data (500 MHz, CDCl$_3$) δ ppm 0.90 (s, 3H), 0.97 (s, 3H), 1.03 (m, 1H), 1.17 (s, 3H), 1.31 (s, 3H), 1.40 (s, 3H), 1.68 (m, 1H), 1.70 (m, 3H), 1.80 (m, 1H), 1.83 (m, 1H), 2.01 (m, 1H), 2.12 (s, 3H), 2.16 (s, 1H), 2.21 (m, 1H), 2.38 (m, 1H), 2.83 (m, 1H), 3.63 (s, 3H), 4.68 (t, J=2.6 Hz, 1H), 5.85 (s, 1H), 10.14 (s, 1H); $^{13}$C NMR (200 MHz, CDCl$_3$) δ ppm 16.4 (CH$_3$, C-20), 16.9 (CH$_2$, C-6), 18.8 (CH$_3$, C-21), 19.5 (CH$_3$, C-22), 19.8 (CH$_3$, C-18), 21.3 (CH$_3$, C-25), 21.3 (CH$_3$, C-27), 23.3 (CH$_2$, C-2), 26.5 (CH$_3$, C-24), 27.8 (CH$_2$, C-1), 30.8 (CH$_2$, C-7), 36.9 (C, C-4), 38.6 (C, C-8), 47.7 (CH, C-5), 52.0 (CH$_3$, C-28), 52.2 (C, C-10), 53.5 (CH, C-9), 60.8 (C, C-13), 70.4 (C, C-14), 72.1 (C, C-16), 76.8 (CH, C-3), 133.0 (C, C-12), 126.4 (CH, C-11), 167.3 (C, C-19), 170.6 (C, C-26), 204.4 (CH, C-23), 206.7 (C, C-17), 210.6 (C, C-15).

Conclusions

Citreohybriddione D (1) was isolated from the HDACi treatment extract. Initial investigation via HPLC of similar fractions indicated that 1 may have also been present in the DNMTi extract as well, but appeared absent in the control treatment fractions. However, HRESIMS investigation of the ethyl acetate partitions of all three treatment extracts revealed that 1 could be found in all treatments. Nevertheless, HRESIMS and NMR analysis shows that there are notable chemical differences between the control and modified conditions, indicating that there may be many other new compounds to be found from this *Penicillium* sp. yet.

The culture optimization of KML12-14MG-B2a was not completed due to time restraints. This organism remains active in the small scale, and warrants further study to be able to replicate that activity on a culture scale that allows for chemical investigation of the active compound(s). The isolation of 1 confirms that this *Penicillium* sp. contains PKSs (polyketide synthases) that are capable of producing interesting secondary metabolites. Additionally, the small scale screening results confirm that this organism responds favorably to HDACi treatment, indicating that efforts in culture optimization would likely be rewarded with the production of many otherwise silenced natural products.

While there are no reported activities for any of the citreohybriddiones (including 1) against human disease, further testing of this new compound is warranted. Due to mass limitations, 1 was only screened against the ESKAPE pathogens and the *Leishmania donovani* parasite. Feeding studies and cytotoxicity profiling are needed to determine how it compares to the rest of the compounds in this class.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating *Leishmania donovani* in a patient comprising:

administering an effective amount of a Phomopsichromin compound, wherein the Phomopsichromin compound has one -continued or

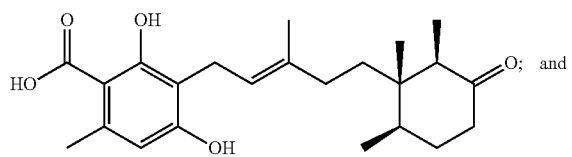

a pharmaceutically acceptable carrier.

2. The method of claim 1, wherein the Phomopsichromin compound has the formula:

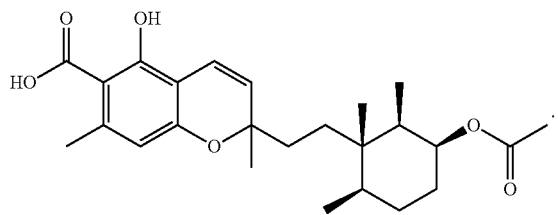 [SMILES: CC(=O)O[C@H]1CC[C@@H](C)[C@](C)(CCC2(C)C=Cc3c(cc(C)c(C(=O)O)c3O)O2)[C@H]1C]

3. A method of inhibiting microbial activity in at least one cell comprising:

contacting the at least one cell with an effective amount of a Phomopsichromin compound, wherein the Phomopsichromin compound has one of the following formulae:

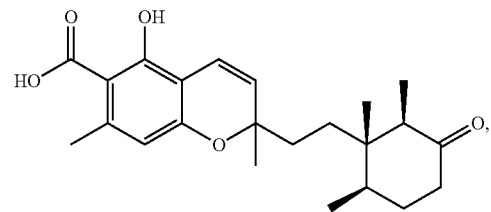

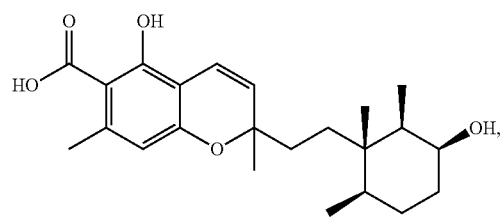

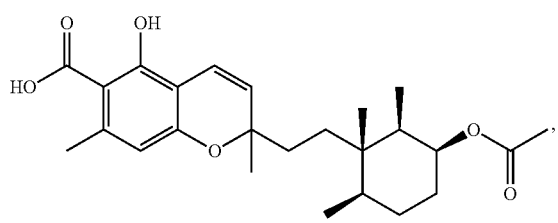

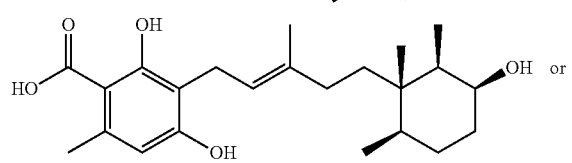

-continued

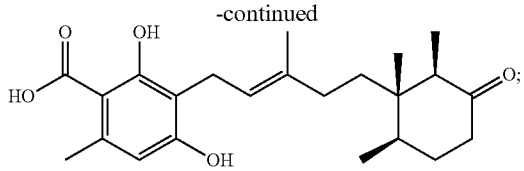

wherein the microbial activity is caused by *Mycobacterium tuberculosis*, *Clostridium difficile*, *Naegleria fowleri*, *Enterococcus faecium*, *Staphylococcus aureus*, *Klebsiella pneumoniae*, *Acinetobacter baumannii*, *Pseudomonas aeruginosa*, or *Enterobacter cloacae*.

4. The method of claim 3, wherein the *Staphylococcus aureus* is methicillin-resistant *Staphylococcus aureus* (MRSA).

5. The method of claim 4, wherein the Phomopsichromin compound has the formula:

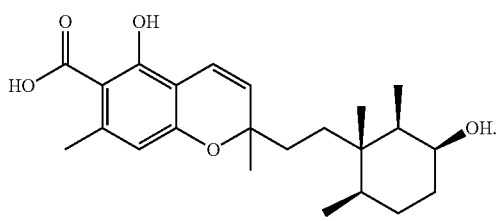 [SMILES: Cc1cc2c(c(O)c1C(=O)O)C=CC(C)(CC[C@@]1(C)[C@H](C)CC[C@H](O)[C@@H]1C)O2]

6. A method of treating a microbial infection in a patient comprising:

administering an effective amount of a Phomopsichromin compound, wherein the Phomopsichromin compound has one of the following formulae:

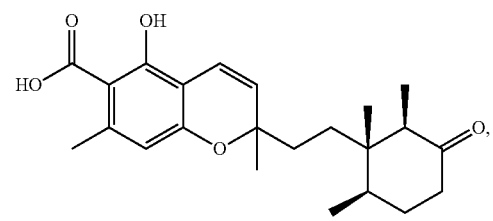

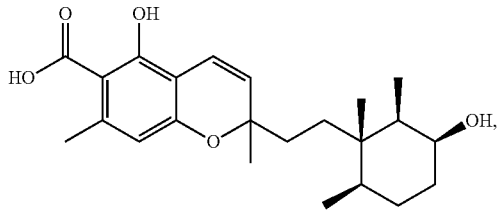 [SMILES: Cc1cc2c(c(O)c1C(=O)O)C=CC(C)(CC[C@@]1(C)[C@H](C)CC[C@H](O)[C@@H]1C)O2]

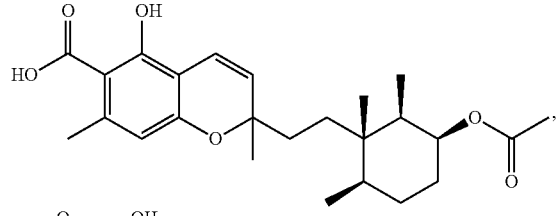

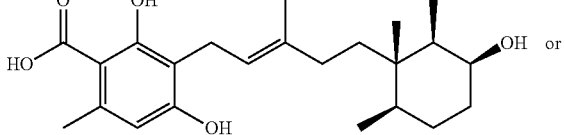

-continued

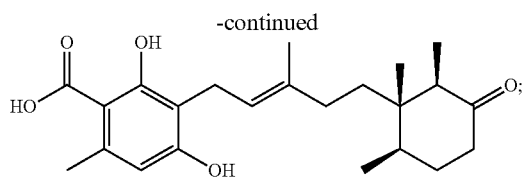

and
a pharmaceutically acceptable carrier;
wherein the microbial infection is caused by *Mycobacterium tuberculosis, Clostridium Difficile, Naegleria Fowleri, Enterococcus Faecium, Staphylococcus Aureus, Klebsiella Pneumoniae, Acinetobacter Baumannii, Pseudomonas Aeruginosa,* or *Enterobacter cloacae.*

7. The method of claim 6, wherein the *Staphylococcus aureus* is methicillin-resistant *Staphylococcus aureus* (MRSA).

8. The method of claim 7, wherein the Phomopsichromin compound has the formula:

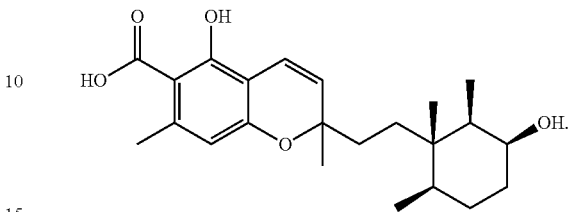

* * * * *

SEQUENCE LISTING

```
<160> NUMBER OF SEQ ID NOS: 7

<210> SEQ ID NO 1
<211> LENGTH: 80
<212> TYPE: DNA
<213> ORGANISM: artificial sequence
<220> FEATURE:
<223> OTHER INFORMATION: BB11-2 forward primer
<220> FEATURE:
<221> NAME/KEY: misc_feature
<222> LOCATION: (1)..(13)
<223> OTHER INFORMATION: n can be a, c, t or g

<400> SEQUENCE: 1
nnnnnnnnnn nnnttggttt ctaggaccgc cgtaatgatt aatagggaca gtcgggggca      60
tcagtattca atcgtcagag                                                  80

<210> SEQ ID NO 2
<211> LENGTH: 80
<212> TYPE: DNA
```

<213> ORGANISM: artificial sequence
<220> FEATURE:
<223> OTHER INFORMATION: BB11-2 forward primer

<400> SEQUENCE: 2

```
gtgaaattct tggatcgatt gaagactaac tactgcgaaa gcatttgcca aggatgtttt    60
cattaatcag gaacgaaagt                                                80
```

<210> SEQ ID NO 3
<211> LENGTH: 80
<212> TYPE: DNA
<213> ORGANISM: artificial sequence
<220> FEATURE:
<223> OTHER INFORMATION: BB11-2 forward primer
<220> FEATURE:
<221> NAME/KEY: misc_feature
<222> LOCATION: (65)..(65)
<223> OTHER INFORMATION: n can be a, c, t or g

<400> SEQUENCE: 3

```
taggggatcg aaaacgatca gataccgttg tagtcttaat cataaactat gcccactagg    60
gatcnggcgg tgttatttct                                                80
```

<210> SEQ ID NO 4
<211> LENGTH: 80
<212> TYPE: DNA
<213> ORGANISM: artificial sequence
<220> FEATURE:
<223> OTHER INFORMATION: BB11-2 reverse primer
<220> FEATURE:
<221> NAME/KEY: misc_feature
<222> LOCATION: (1)..(15)
<223> OTHER INFORMATION: n can be a, c, t or g
<220> FEATURE:
<221> NAME/KEY: misc_feature
<222> LOCATION: (17)..(17)
<223> OTHER INFORMATION: n can be a, c, t or g
<220> FEATURE:
<221> NAME/KEY: misc_feature
<222> LOCATION: (19)..(19)
<223> OTHER INFORMATION: n can be a, c, t or g
<220> FEATURE:
<221> NAME/KEY: misc_feature
<222> LOCATION: (22)..(22)
<223> OTHER INFORMATION: n can be a, c, t or g

<400> SEQUENCE: 4

```
nnnnnnnnnn nnnnncngnt cncccttgt ggtgcccttc cgtcaatttc tttaagtttc     60
agccttgcga ccatactccc                                                80
```

<210> SEQ ID NO 5
<211> LENGTH: 80
<212> TYPE: DNA
<213> ORGANISM: artificial sequence
<220> FEATURE:
<223> OTHER INFORMATION: BB11-2 reverse primer

<400> SEQUENCE: 5

```
cccagaaccc aaaaacttta ctttcgtgta aggtgccgag cgggtcaaga aataacaccg    60
cccgatccct agtcggcata                                                80
```

<210> SEQ ID NO 6
<211> LENGTH: 80
<212> TYPE: DNA
<213> ORGANISM: artificial sequence
<220> FEATURE:
<223> OTHER INFORMATION: BB11-2 reverse primer

```
<220> FEATURE:
<221> NAME/KEY: misc_feature
<222> LOCATION: (42)..(42)
<223> OTHER INFORMATION: n can be a, c, t or g
<220> FEATURE:
<221> NAME/KEY: misc_feature
<222> LOCATION: (64)..(64)
<223> OTHER INFORMATION: n can be a, c, t or g
<220> FEATURE:
<221> NAME/KEY: misc_feature
<222> LOCATION: (66)..(66)
<223> OTHER INFORMATION: n can be a, c, t or g
<220> FEATURE:
<221> NAME/KEY: misc_feature
<222> LOCATION: (69)..(69)
<223> OTHER INFORMATION: n can be a, c, t or g

<400> SEQUENCE: 6
gtttatggtt aagactacaa cggtatctga tcgttttcga tnccctaact ttcgttcctg      60
attnangana acatccttgg                                                  80

<210> SEQ ID NO 7
<211> LENGTH: 40
<212> TYPE: DNA
<213> ORGANISM: artificial sequence
<220> FEATURE:
<223> OTHER INFORMATION: BB11-2 reverse primer
<220> FEATURE:
<221> NAME/KEY: misc_feature
<222> LOCATION: (13)..(13)
<223> OTHER INFORMATION: n can be a, c, t or g
<220> FEATURE:
<221> NAME/KEY: misc_feature
<222> LOCATION: (15)..(15)
<223> OTHER INFORMATION: n can be a, c, t or g
<220> FEATURE:
<221> NAME/KEY: misc_feature
<222> LOCATION: (20)..(21)
<223> OTHER INFORMATION: n can be a, c, t or g
<220> FEATURE:
<221> NAME/KEY: misc_feature
<222> LOCATION: (23)..(23)
<223> OTHER INFORMATION: n can be a, c, t or g
<220> FEATURE:
<221> NAME/KEY: misc_feature
<222> LOCATION: (28)..(28)
<223> OTHER INFORMATION: n can be a, c, t or g

<400> SEQUENCE: 7
gaaatgcttt ccnantaatn ngncttcnat caaatcctca                            40
```